United States Patent
Cook et al.

(12)

(10) Patent No.: US 6,270,952 B1
(45) Date of Patent: Aug. 7, 2001

(54) METHODS FOR QUENCHING PATHOGEN INACTIVATORS IN BIOLOGICAL MATERIALS

(75) Inventors: David Cook, Lafayette; Adonis Stassinopoulos, Dublin, both of CA (US)

(73) Assignee: Cerus Corporation, Concord, CA (US)

( * ) Notice: Subject to any disclaimer, the term of this patent is extended or adjusted under 35 U.S.C. 154(b) by 0 days.

(21) Appl. No.: 09/110,776

(22) Filed: Jul. 6, 1998

Related U.S. Application Data
(60) Provisional application No. 60/070,597, filed on Jan. 6, 1998.

(51) Int. Cl.[7] ....................................................... A01N 1/02
(52) U.S. Cl. .................................. 435/2; 435/1.1; 422/28; 422/30; 422/44
(58) Field of Search ........................... 435/2, 1.1; 422/28, 422/30, 44

(56) References Cited

U.S. PATENT DOCUMENTS

| | | |
|---|---|---|
| 2,402,665 | 6/1946 | Peppel et al. . |
| 4,252,645 | 2/1981 | Marconi et al. . |
| 4,337,269 | 6/1982 | Berke et al. . |
| 4,727,027 | 2/1988 | Wiesehahn et al. . |
| 4,748,120 | 5/1988 | Wiesehahn . |
| 4,944,920 | 7/1990 | Rubinstein . |
| 4,971,760 | 11/1990 | Rubinstein . |
| 5,055,485 | 10/1991 | Geacintov et al. . |
| 5,094,960 | 3/1992 | Bonomo . |
| 5,120,649 | 6/1992 | Horowitz et al. . |
| 5,232,844 | 8/1993 | Horowitz et al. . |
| 5,281,579 | 1/1994 | Estep . |
| 5,418,130 | 5/1995 | Platz et al. . |
| 5,559,250 | 9/1996 | Cook et al. . |
| 5,587,490 | 12/1996 | Goodrich, Jr. et al. . |
| 5,591,350 | 1/1997 | Piechocki et al. . |
| 5,601,730 | 2/1997 | Page et al. . |
| 5,637,451 | 6/1997 | Ben-Hur et al. . |
| 5,658,722 | 8/1997 | Margolis-Nunno et al. . |
| 5,660,731 | 8/1997 | Piechocki et al. . |
| 5,691,132 | 11/1997 | Wollowitz et al. . |
| 5,753,258 | 5/1998 | Schreier et al. . |
| 6,093,725 * | 7/2000 | Cook et al. ........................... 514/297 |

FOREIGN PATENT DOCUMENTS

| | | |
|---|---|---|
| 0 352 076 A2 | 1/1990 | (EP) . |
| 0 352 076 B1 | 1/1990 | (EP) . |
| 0 457 196 A2 | 11/1991 | (EP) . |
| 0 641 796 A1 | 3/1995 | (EP) . |
| WO 95/00631 WO | 1/1995 | (WO) . |
| 96/02838A1 * | 2/1996 | (WO) . |
| WO 96/09846 | 4/1996 | (WO) . |
| WO 96/14737 | 5/1996 | (WO) . |
| WO 96/39816 | 12/1996 | (WO) . |
| WO 96/39818 | 12/1996 | (WO) . |
| WO 96/40857 | 12/1996 | (WO) . |
| WO 97/02028 | 1/1997 | (WO) . |
| WO 97/07674 | 3/1997 | (WO) . |
| WO 97/16966 | 5/1997 | (WO) . |
| WO 97/18844 | 5/1997 | (WO) . |
| WO 98/30545 * | 7/1998 | (WO) . |
| WO 99/34839 * | 7/1999 | (WO) . |

OTHER PUBLICATIONS

Gourdie, T. A. (1991). "Synthesis and Evaluation of DNA–Targeted Spatially Separated Bis(aniline mustards) as Potential Alkylating Agents with Enhanced DNA Cross–Linking Capability," *J. Med. Chem.* 34(1):240–248.

Aejmelaeus et al., "Is there an unidentified defence mechanism against infection in human plasma?", (1996) *FEBS Letters* 384:128–130.

Al–Harbi et al., "Gentamycin and cyclosporine increase total soluble thiols in the plasma and lymphocytes of rats and perturb erythrocyte ragility", (1997) *Med Sci Res* 25:155–157.

Awasthi et al., "Purification and Characterization of a New Form of Glutathione S–Transferase from Human Erythrocytes", (1984) *Biochemical and Biophysical Research Communications* 125:1053–1060.

Baxt et al, "Mechanisms of Vesicular Stomatitis Virus–Induced Cytopathic Effects", (1976) *Virology* 72:383–392.

Begleiter et al., "Chlorambucil in Chronic Lymphocytic Leukemia: Mechanism of Action", (1996) *Leukemia and Lymphoma* 23: 187–201.

(List continued on next page.)

*Primary Examiner*—Francisco Prats
(74) *Attorney, Agent, or Firm*—Morrison & Foerster LLP; John W. Tessman

(57) ABSTRACT

Methods are provided for quenching undesired side reactions of pathogen inactivating compounds in biological materials. In a particular embodiment, methods are provided for quenching undesired side reactions of a pathogen inactivating compound that includes a functional group which is, or which is capable of forming, an electrophilic group. In this embodiment, the material is treated with the pathogen inactivating compound and a quencher, wherein the quencher comprises a nucleophilic functional group that is capable of covalently reacting with the electrophilic group. The electrophilic group on the pathogen inactivating compound is preferably a non-radical cationic group. In one embodiment, the pathogen inactivating compound includes a nucleic acid binding ligand and a mustard group, wherein the mustard group is capable of reacting in situ to form the electrophilic group. Preferred quenchers are thiols, such as glutathione. Biological materials which may be treated include whole blood, red blood cells, blood plasma, and platelets. The methods permit inhibition of the modification of red blood cells in red blood cell containing materials during pathogen inactivation.

117 Claims, 1 Drawing Sheet

OTHER PUBLICATIONS

Beutler et al., "The Role of Bone Marrow Transplantation in the Treatment of Acute Leukemia in Remission", (1982) *Blood* 59:1115–1117.

Bolton et al., "Kinetic analysis of the reaction of melphalan with water, phosphate, and glutathione", (1993) *Drug Metab Dispos* 21:986–996.

Bolton et al., "Specificity of Isozymes of Murine Hepatic Gluthathione S–Transferase for the Conjugation of Glutathione with L–Phenylalanine Mustard", (1991) *Cancer Research* 51:2410–2415.

Bonadonna et al., "Protection studies with sodium thiosulfate against methyl bis (β–chloroethyl)amine hydrochloride (HN2) and its ethylenimonium derivative", (1964) *Clinical Pharmacology and Therapeutics* 6:50–64.

Budowsky et al. "Principles of Selective Inactivation of the Viral Genome: Dependence of the Rate of Viral RNA Modification on the Number of Protonizable Groups in Ethyleneimine Oligomers", (1996) *Vaccine Research* 5:29–39.

Chong et al., "Evaluation of Thiol Borth for the Culture of *Salmonella typhi* and Other Bacteria from Blood", *Yonsei Medical Journal,* (1990) 31:163–167.

Colvin et al., "Role of glutathione in cellular resistance to alkylating agents", (1993) *Adv Enzyme Regul* 33:19–26.

Colvin et al., "Alkylating Properties of Phosphoramide Mustard", (1976) *Cancer Res* 36:1121–1126.

Davey et al., "The effect of prestorage irradiation on post-transfusion red cell survival", (1992) *Transfusion* 32:525–528.

Dern et al., "Studies on the preservation of human blood. II. The relationship of erythrocyte adenosine triphosphate levels and other in vitro measures to red cell storageability", (1967) *J Lab & Clin Med* 69:968–978.

Dirr et al., "X–ray crystal structures of cytosolic glutathione S–transferases implications for protein architecture, substrate recognition and catalytic function", *Eur J Biochem* (1994) 220: 645–661.

Dirven et al., "Glutathione Conjugation of Alkylating Cytostatic Drugs with a Nitrogen Mustard Group and the Role of Glutathione S–Transferases", (1996) *Chem Res Toxicol* 9:350–360.

Dirven et al., "Glutathione Conjugation of the Cytostatic Drug Ifosfamide and the Role of Human Glutathione S–Transferases", (1995) *Chem Res Toxicol* 8:979–986.

Dirven et al., "The interaction of glutatione with 4–hydroxycyclophosphamide and phosporamide mustard, studies by 31P nuclear magnetic resonance spectroscopy", (1994) *Chem Bio Interact* 93:185–196.

Dirven et al., "The Role of Human Glutathione S–Transferases Isoenzymes in the Formation of Glutathione Conjugates of the Alkylating Cytostatic Drug Tiotepa", (1995) *Cancer Res*:55:1701–1706.

Dorr, R.T., "Chemoprotectants for Cancer Chemotherapy", (1991) *Semin Oncol* 18:48–58.

Dulik et al., "Characterization of Glutathione Conjugates of Chlorambucil by Fast Atom Bombardment and Thermospray Liquid Chromatography/Mass Spectrometry", (1990) *Biomed Environ Mass Spectrom* 19:248–252.

Dulik et al., "Characterization of melphalan–glutatione adducts whose formation is catalyzed by glutathione transferases", (1986) *Biochem Pharmacol.* 35:3405–3409.

Dulik et al., "Conversion of Melphalan to 4–(Glutathionyl)Phenylalanine. A Novel Mechanism for Conjugation by Glutathione–S–transferases", (1987) *Drug Metab Dispos* 15:195–199.

Fasth et al., "Protective Effect of Thiosulfate and Metabolic Thiosulfate Precursors Against Toxicity of Nitrogen Mustard ($HN_2$)", (1973) *Biochem Pharmacology* 22:1337–1351.

Gamcsik et al., "Kinetics of the conjugation of aniline mustards with glutathione and thiosulfate", (1997) *Chem Biol Interact* 105:35–52.

Gao et al., "A Novel Cationic Liposome Reagent for Efficient Transfection of Mammalian Cells", (1991) *Biochem Biophys Res Commun* 179:280–285.

Gao et al., "Cytoplasmic expression of a reporter gene by co–delivery of T7 RNA polymerase and T7 promoter sequence with cationic liposomes", (1993) *Nucleic Acids Res* 21:2867–2872.

Gao et al., "Potentiation of Cationic Liposome–Mediated Gene Delivery by Polycations", (1996) *Biochemistry* 35:1027–1036.

Greenwalt et al., "Studies in Red Blood Cell Preservation: 3. A Phosphate–Ammonium–Adenine Additive Solution", (1990) *Vox Sang* 58:94–99.

Guenther et al., "Direct Measurement of Melphalan Conjugation with Glutathione: Studies with Human Melanoma Cells and Mammalian Liver", (1992) *J Pharmacol Exp Ther* 260:1331–1336.

"Guidelines for Prevention of Transmission of Human Immunodeficiency Virus and Hepatitis B Virus to Health–Care and Public–Safety Workers", (Jun. 23, 1989) *Morbidity and Mortality Weekly Report, Centers for Disease Control,* Atlanta, Georgia, vol. 38, No. S–6, pp. 1; 3–37. (Page 2 blank).

Hageman et al., "Reducing Effects of Garlic Constituents on DNA Adduct Formation in Human Lymphocytes In Vitro", (1997) *Nutrition and Cancer* 27:177–185.

Hanson et al., "Application of a Rapid Microplaque Assay for Determination of Human Immunodeficiency Virus Neutralizing Antibody Titers", (1990) *J. Clin Microbio* 28:2030–2034.

Högman et al., "Storage of saline–adenine–glucose–mannitol–suspended red cells in a new plastic container: polyvinylchloride plasticized with butyryl–n–trihexyl–citrate", (1991) *Transfusion* 31:26–29.

Högman et al., "Half–Strength Citrate CPD Combined with a New Additive Solution for Improved Storage of Red Blood Cells Suitable for Clinical Use", (1993) *Vox Sang* 65:271–278.

"γIrradiation of Cellular Blood Components for Prevention of TA–GVHD", *Clinical Practice of Transfusion Medicine* (Graft–Versus Host Disease), pp. 939–940. (1997).

Kawabata et al., "Mechanisms of in vitro immunosuppression by hepatocyte–generated cyclophosphamide metabolites and 4–hyperoxycyclophosphamide", (1990) *Biochem Pharmacol* 40:927–935.

Koch et al., "Effects of N–acetylcysteine on bacterial clearance", (1996) *European Journal of Clinical Investigation* 26:884–892.

Lasic, D. D., "Liposomes" *Liposomes in Gene Delivery,* (1997) CRC Press, Boca Raton, FL, Chapter 6, pp. 67–112.

LoGrippo et al., Chemical and Combined Methods for Plasma Sterilization–Proceedings of the Sixth Congress of the International Society of Blood Transfusion, (1958) Bibliotheca Haematologica (Hollander, ed.), pp. 225–230.

Malmberg et al., "Effect of increased blood–oxygen affinity on oxygen transport in hemorrhagic shock", (1979) *J Appl Physiol Respirat Environ Exercise Physiol* 47:889–895.

Mangels et al., "Quantitative Evaluation of Three Commercial Blood Culture Media for Growth of Anaerobic Organisms", (1978) *Journal of Clinical Microbiology* 7:59–62.

Marcus et al., "Cell Killing by Viruses: 1. Comparison of Cell–Killing, Plaque–Forming, and Defective–Interfering Particles of Vesicular Stomatitis Virus", (1974) *Virology* 57:321–338.

Mulder et al., "Modulation of glutathione conjugation in vivo: how to decrease glutathione conjugation in vivo or in intact cellular systems in vitro", (1997) *Chem Biol Interact* 105:17–34.

Popovic et al., "Detection, Isolation, and Continuous Production of Cytopathic Retroviruses (HTLV–III) from Patients with AIDS and Pre–AIDS", (1984) *Science* 224:497–500.

Roth, Jr., et al., "Survival Rates and Properties of Sickle Cell Anemia Red Cells Treated with Nitrogen Mustard", (1987) *Pathophysiological Aspects of Sickle Cell Vaso–Occlusion*, pp. 245–261.

Rywkin et al., "Importance of Type I and Type II Mechanisms in the Photodynamic Inactivation of Viruses in Blood with Aluminum Phthalocyanine Derivatives", (1992) *Photochemistry and Photobiology* 56:463–469.

Simon, "Adenine in Blood Banking", (1977) *Transfusion* 17:317–325.

"Special Reagents for Thiol Groups", (1971) *Aldrichimica acta*, Aldrich Chemical Company, Inc., (Publisher) 4:33–35, 46–48.

Szinicz et al., "Effect of Various Compounds on the Reaction of Tris–(2–Chloroethyl)amine with Ribonucleic Acid in vitro and on its Toxicity in Mice", (1981) *Arzneimittel–Forschung* 31:1713–1717.

Tew, "Glutathione–associated Enzymes in Anticancer Drug Resistance", (1994) *Cancer Research* 54:4313–4320.

Wagner et al., "Red cell alterations associated with virucidal methylene blue phototreatment", (1993) *Transfusion* 33:30–36.

Watson et al., "Kinetics of Phosphormide Mustard Hydrolysis in Aqueous Solution", *J. Pharm Sci* 74:1283–1292 (1985).

Wedner et al., "Inhibition of Lectin–Induced Lymphocyte Activation by 2–Cyclohexene–1–One: Analysis of DNA Synthesis in Individual Cells by BUdR Quenching of Hoechst 33258", (1985) *Int J Immunopharmac* 7:25–30.

Weinberg et al., "Effectiveness of the Antimicrobial Removal Device, BACTEC 16B Medium, and Thiol Broth in Neutralizing Antibacterial Activities of Imipenem, Norfloxacin, and Related Agents", (1984) *Journal of Clinical Microbiology* 19:207–209.

Woodson, Robert D., "Physiological significance of oxygen dissociation curve shifts", *Critical Care Medicine* 7:368–373.

Yuan et al., "Glutatione Conjugation with Phosphoramide Mustard and Cyclophosphamide. A Mechanistic Study Using Tandem Mass Spectrometry", (1991) *Drug Metab Dispos.* 19:625–629.

* cited by examiner

METHODS FOR QUENCHING PATHOGEN INACTIVATORS IN BIOLOGICAL MATERIALS

CROSS-REFERENCE TO RELATED APPLICATIONS

This application claims the benefit of U.S. Provisional Application Ser. No. 60/070,597, filed Jan. 6, 1998, the disclosure of which is incorporated herein by reference.

TECHNICAL FIELD

This application relates to methods of treating biological materials, such as blood products, with a nucleophilic compound to quench reactive electrophilic compounds in the material.

BACKGROUND ART

The transmission of disease by blood products and other biological materials remains a serious health problem. While significant advances in blood donor screening and blood testing have occurred, viruses such as hepatitis B (HBV), hepatitis C (HCV), and human immunodeficiency virus (HIV) may escape detection in blood products during testing due to low levels of virus or viral antibodies. In addition to the viral hazard, there are currently no licensed tests to screen for the presence of bacteria or protozoans in blood intended for use in transfusions. The risk also exists that a hitherto unknown pathogen may become prevalent in the blood supply and present a threat of disease transmission, as in fact occurred before the recognition of the risk of HIV transmission via blood transfusions.

Exposure of laboratory workers to blood or other body fluids also presents a health hazard. As recently as 1989, the Centers for Disease Control estimated that twelve thousand health-care workers whose jobs involve exposure to blood are infected with hepatitis B virus each year. "Guidelines for Prevention of Transmission of Human Immunodeficiency Virus and Hepatitis B Virus to Health-Care and Public-Safety Workers," Morbidity and Mortality Weekly Report, vol. 38, no. S-6, June 1989. This statistic illustrates the need for methods to inactivate pathogens in biological materials.

Chemical agents have been introduced into blood or blood plasma to inactivate pathogens prior to clinical use of the blood product. Methods and compositions for photochemical inactivation of pathogens have been described. U.S. Pat. Nos. 5,587,490 and 5,418,130 describe substituted psoralens used for photochemically inactivating viral or bacterial contaminants in body fluids. Phenothiazines such as methylene blue have been shown to inactivate pathogens in blood products upon illumination. Wagner et al., Transfusion, 33: 30–36(1993). U.S. Pat. No. 5,637,451 describes a method for inactivating viruses in a red blood cell containing material by adding a phthalocyanine compound and irradiating the material.

The disadvantage of photochemical methods for pathogen inactivation is that the reactive free radicals and oxygen species that are generated also can cause damage to blood products and compromise their suitability for their intended use. Free radical quenchers have been used in the photochemical methods for pathogen inactivation, to reduce and minimize free radical damage which occurs during the photochemical reaction, as described in U.S. Pat. Nos. 4,727,027, 5,587,490, 5,418,130, 5,232,844, 5,658,722 and 5,637,451, and International Patent Application WO 97/16966.

Compounds have been developed for pathogen inactivation which do not require photoactivation. These compounds are typically electrophiles that react with pathogens. For example, U.S. Pat. No. 5,055,485 describes the inactivation of viruses in cell and protein containing compositions using aryl diol epoxides. Other compounds generate electrophiles in situ. LoGrippo el al. evaluated the use of nitrogen mustard, $CH_3$—$N(CH_2CH_2Cl)_2$, for viral inactivation. LoGrippo et al., Proceedings of the Sixth Congress of the International Society of Blood Transfusion, Bibliotheca Haematologica (Hollander, ed.), 1958, pp. 225–230. More significantly, U.S. Pat. Nos. 5,691,132 and 5,559,250, the disclosures of which are incorporated herein by reference, describe the use of N1,N1-bis(2-chloroethyl)-N4-(6-chloro-2-methoxy-9-acridinyl)-1,4-pentanediamine ("quinacrine mustard") and 5-[N,N-bis(2-chloroethyl)amino]methyl-8-methoxypsoralen for pathogen inactivation in blood, blood products, and a variety of samples of biological origin. Pathogen inactivating compounds which include an aziridine covalently attached to a polyamine moiety also have been used, as described in Budowsky et al., Vaccine Research 5: 29–39 (1996).

Ideally, addition of the pathogen inactivating compounds that inactivate by electrophilic reactions or intermediates to the blood product or other biological sample would inactivate pathogens without causing any undesirable modifications to the sample. The pathogen inactivating compounds react with pathogens by an electrophilic process, and do not require photoactivation. Therefore reactive oxygen or free radical species are not produced, and oxidative damage is not a concern. Other undesirable side reactions, however, may occur. For example, electrophilic reactions with different biological materials, including proteins may occur. These side reactions can potentially compromise use of the biological sample for its intended purpose.

Thus, there is a need for methods to prevent unwanted electrophilic side reactions of pathogen inactivating compounds that interact with pathogens electrophilically, while preserving the ability of the pathogen inactivating compound to inactivate harmful pathogens. There is a need for methods of inactivating pathogens in biological materials while reducing undesired side reactions.

DISCLOSURE OF THE INVENTION

Methods are provided for quenching compounds comprising reactive groups in materials. A variety of compounds may be quenched in materials, such as biological materials, using the methods disclosed herein. Compounds that may be quenched include compounds that comprise a functional group that is, or which is capable of forming, and has formed, in situ, a reactive group such as an electrophilic group. For example, the functional group may be a mustard group that is capable of forming in situ a reactive group such as an electrophilic aziridine, aziridinium, thiirane or thiiranium ion. In another embodiment, the functional group may be an epoxide.

In one embodiment, methods are provided for quenching side reactions of pathogen inactivating compounds used to inactivate pathogens in biological materials. In a particular embodiment, methods are provided for quenching undesired side reactions of a pathogen inactivating compound that includes a functional group which is, or which is capable of forming, an electrophilic group. In this embodiment, a biological material is treated with the pathogen inactivating compound and a quencher comprising a nucleophilic functional group that is capable of covalently reacting with the electrophilic group. The electrophilic group on the pathogen inactivating compound is in one preferred embodiment a cationic group. Biological materials can be treated with the pathogen inactivating compound and the quencher, for example, in vitro or ex vivo. In a preferred embodiment, the pathogen inactivating compound and the quencher are administered to a material in an effective amount for the pathogen inactivating compound to inactivate pathogens in the material while also permitting the quencher to quench undesired side reactions of the pathogen inactivating compound.

In one embodiment, a quencher may be introduced into a multiphase system, such as a two phase system. For example, the quencher may be administered to a two phase system wherein a membrane separates the first and second phases. In one embodiment, one phase is bounded by the membrane. For example, the membrane may define the exterior membrane of a pathogenic organism, the first phase may be the phase in which the pathogenic organism is contained, and the second phase may be the interior of the pathogenic organism. The membrane may be, for example the lipid coat of a virus, the first phase may be a fluid in which the virus is disposed, such as blood, and the second phase may be the interior of the virus comprising viral nucleic acids. In another embodiment, the membrane may be a cell membrane, and the membrane bounded phase may be the interior of a pathogenic unicellular organism, such as a bacterium. In this embodiment, a pathogen inactivating compound is introduced into the two phase system that preferably is kinetically or thermodynamically capable of traversing the membrane, while the quencher substantially is not kinetically or thermodynamically capable of traversing the membrane, relative to the pathogen inactivating compound.

In one embodiment, a method is provided for quenching undesired side reactions of a pathogen inactivating compound in a two phase biological material comprising a first liquid phase having a pathogen comprising a membrane therein, and a second phase bounded by the membrane of the pathogen. The second phase thus is the contents contained within the pathogen membrane. The biological material is treated with a pathogen inactivating compound comprising a functional group which is capable of forming an electrophilic group. Prior to, contemporaneously, or after treatment with the pathogen inactivating compound, the biological material is treated with a quencher comprising a nucleophilic group that is capable of covalently reacting with the electrophilic group. Preferably, the quencher is added prior to or contemporaneously with the pathogen inactivating compound. Preferably, the pathogen inactivating compound is kinetically or thermodynamically capable of traversing the membrane, prior to formation of the electrophilic group. Preferably, the rate of membrane penetration by the pathogen inactivating compound is substantially reduced after formation of the electrophilic group, relative to the pathogen inactivating compound prior to formation of the electrophilic group. Preferably, the pathogen inactivating compound is substantially not kinetically or thermodynamically capable of traversing the membrane after formation of the electrophilic group, relative to the pathogen inactivating compound prior to formation of the electrophilic group. The quencher preferably is substantially not kinetically or thermodynamically capable of traversing the membrane, relative to the pathogen inactivating compound prior to the formation of the electrophilic group. The quencher is permitted to react with the electrophilic group of the pathogen inactivating compound, and the reaction of the quencher with the electrophilic group of the pathogen inactivating compound preferably occurs substantially in the first phase. The pathogen inactivating compound comprising the electrophilic group reacts with a nucleic acid of the pathogen in the second membrane bounded phase, thereby inactivating the pathogen. The methods permit pathogen inactivation by reaction of the pathogen inactivating compound with pathogen nucleic acids within the pathogen membrane, while permitting quenching of reactive pathogen inactivating compounds, as well as reactive species formed therefrom, in the phase in which the pathogen is disposed.

The methods disclosed herein are advantageous, since in the two phase system, the quencher is administered to the first phase and substantially is not capable of traversing the exterior membrane of the pathogen, and thus is substantially not present in the second phase, i.e., the interior of the pathogen. The pathogen inactivating compound is administered, for example, to the first phase, and is capable of traversing the membrane of the pathogen, prior to formation of the electrophilic group. Upon formation of the electrophilic group in situ, the pathogen inactivating compound substantially is no longer capable of traversing the membrane. Thus, quenching selectively occurs in the first phase, while in the second phase, i.e., the interior of the pathogen, the pathogen inactivating compound reacts with nucleic acids of the pathogen without quenching. Thus, in a biological material, such as a blood product, quenching of reactive groups on the pathogen inactivating compound and degradation products thereof occurs selectively in the first phase in which the pathogen is suspended. The quenching in the first phase thus reduces unwanted side reactions of the reactive group on the pathogen inactivating compound, such as covalent modification of proteins or cell surfaces in blood. In the method, the pathogen inactivating compound and the quencher are administered in an effective amount to inactivate pathogens in the material while quenching undesired side reactions of the pathogen inactivating compound. The quencher thus has a protective effect in reducing unwanted side reactions in materials such as blood, while permitting pathogen inactivation to occur.

The methods may be used to treat biological materials comprising pathogens, such as prokaryotic and eukaryotic organisms and lipid coated viruses. In particular, the methods may be used to treat pathogens comprising membranes, such as lipid coated viruses, and bacteria that include a membrane in the form of a cell membrane. Exemplary quenchers for treating biological materials, such as blood products, having therein a pathogen comprising a membrane, include glutathione, N-acetylcysteine, cysteine, mercaptoethanesulfonate salts, or dimercaprol.

The pathogen inactivating compound may include a nucleic acid binding ligand and a functional group which is, or which is capable of forming, an electrophilic group, wherein the electrophilic group is capable of reacting with a nucleic acid to form a covalent bond with a nucleic acid. The pathogen inactivating compound also may further include a frangible linker, linking the nucleic acid binding ligand and the functional group. For example, the functional group may be a mustard group which is capable of reacting in situ to form the electrophilic group, such as an aziridinium ion. Exemplary pathogen inactivating compounds include quinacrine mustard, N-(2-chloroethyl)-N-ethyl-N'-(6-chloro-2-methoxy-9-acridinyl)-1,3-propanediamine dihydrochloride, and 5-[N,N-bis(2-chloroethyl)amino]methyl-8-methoxypsoralen. Other pathogen inactivating compounds include compounds comprising an aziridine covalently linked to a polyamine moiety, as described in Budowsky et al., *Vaccine Research*, 5: 29–39 (1996).

Quenchers which may be used may include nucleophilic functional groups such as thiols, thioacids, dithoic acids, phosphates, thiophosphates and amines. Exemplary quenchers include glutathione, N-acetylcysteine, cysteine, thiosulfate, mercaptoethanesulfonate salts, and dimercaprol. In a preferred embodiment, the quencher is glutathione.

In methods wherein a biological material, such as a blood product, is treated with a quencher and a pathogen inactivating compound, the quencher may be added to the material prior to, simultaneously with, or after the addition of the pathogen inactivating compound. Preferably, the quencher is added prior to or contemporaneously with the pathogen inactivating compound. In another preferred embodiment, the quencher is added within about 30 minutes, for example, within about 15–20 minutes, or within about 10 minutes of addition of the pathogen inactivating compound. Biological materials which may be treated include blood products, such as whole blood, red blood cells, blood plasma, or fractions thereof, and platelets. The methods may be used to produce treated blood products that are suitable for introduction into an individual. For example, the treated material may be transfused into an individual in need thereof. Optionally, the concentration of the pathogen inactivating compound and/or quencher in the material may be reduced after the treatment, and before transfusion, for example, by filtration or adsorption. A wide variety of biological materials, such as blood products, that contain, or are suspected to contain, a pathogen may be treated. In one particular embodiment, a method is provided for quenching undesired side reactions of a pathogen inactivating compound in a material comprising red blood cells, wherein the method includes treating a material comprising red blood cells with a pathogen inactivating compound comprising a functional group which is, or which is capable of forming, an electrophilic group, and treating the material with a quencher comprising a nucleophilic group that is capable of covalently reacting with the electrophilic group. The pathogen inactivating compound in one embodiment comprises a nucleic acid binding ligand and a mustard group that is capable of reacting in situ to form an electrophilic group, such as an aziridinium ion. The material may comprise packed red blood cells. The material may comprise, for example, a blood product with a hematocrit of about 30–85%. For example, a material comprising red blood cells may be treated with a pathogen inactivating compound and a quencher, and then the treated material may be transfused into an individual in need thereof.

The concentration of the pathogen inactivating compound may be, for example, about 0.1 $\mu$M to 5 mM. A concentration of pathogen inactivating compound may be provided which is sufficient to inactivate, for example, at least about 3 to 6 logs of a pathogen in the material being treated. The nucleophilic group is preferably a thiol group. The quencher in a preferred embodiment is glutathione. The concentration of glutathione can be, for example, on the order of about 0.5 to 30 mM. The material can be incubated with the pathogen inactivating compound and the quencher, for example, for at least about 1 to 48 hours.

Preferably, the quencher reduces the inactivation of a pathogen by the pathogen inactivating compound by no greater than about 3 logs in comparison to a control pathogen inactivation conducted in the absence of the quencher. In another preferred embodiment, in the method, the quencher reduces the inactivation of a viral pathogen by the pathogen inactivating compound by no greater than about 1 log in comparison to a control pathogen inactivation conducted in the absence of the quencher. Preferably, in the embodiment wherein a material comprising red blood cells is treated, red blood cell function is not substantially altered after the treatment.

In one preferred embodiment, a method is provided, wherein the method comprises treating a red blood cell containing material with an effective amount of the pathogen inactivating compound and the quencher to inactivate at least 2 logs of a pathogen, and wherein red blood cell function is not substantially altered by the treatment. In another preferred embodiment, a method is provided wherein the method comprises treating the material with an effective amount of the pathogen inactivating compound and the quencher to inactivate at least 2 logs of a pathogen, and wherein hemolysis of the red blood cells is less than 3% after 28 days of storage.

BEST MODE FOR CARRYING OUT THE INVENTION

Figure 1:
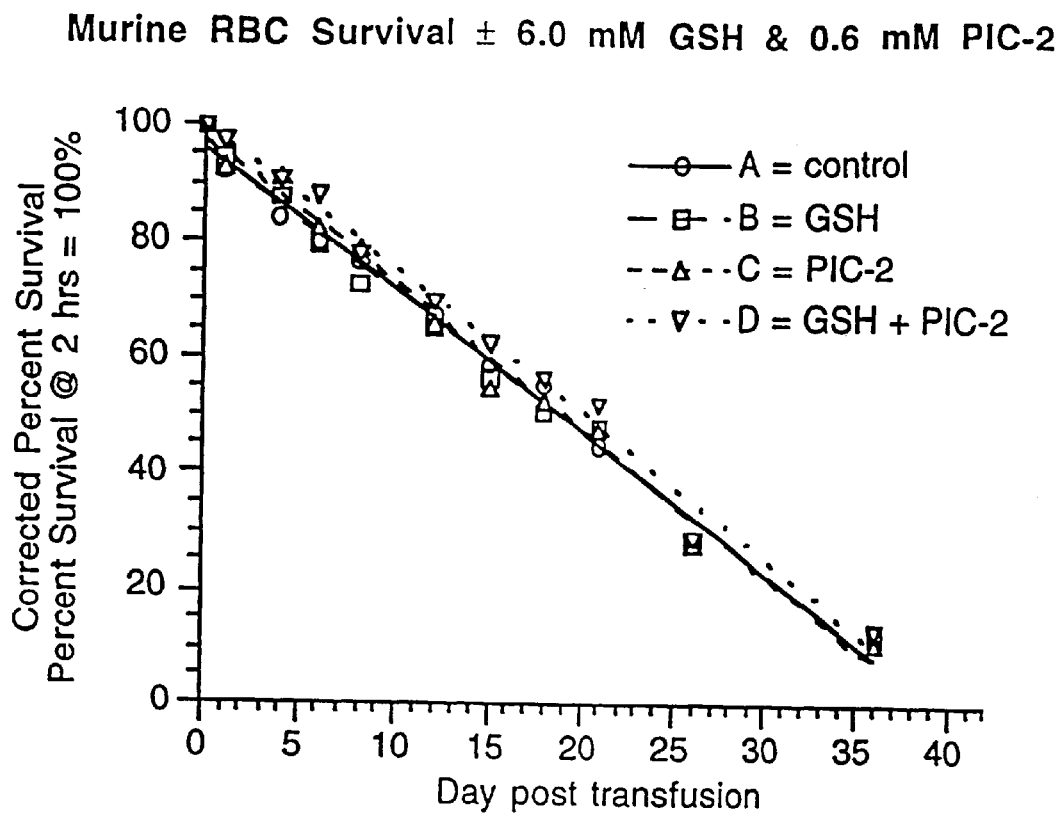
FIG. 1 is a graph showing murine red blood cell survival after treatment with glutathione and a pathogen inactivating compound.

Methods are provided for quenching reactive chemical species, such as compounds comprising electrophilic groups, in materials. In one embodiment, methods are provided for quenching pathogen inactivating compounds in materials, including biological materials, such as blood products. In another embodiment, methods are provided for inhibiting the modification of biological materials, such as red blood cells, that are treated with pathogen inactivating compounds. The pathogen inactivating compound and the quencher are administered in an effective amount to inactivate pathogens in the material while quenching undesired side reactions of the pathogen inactivating compound. The quencher thus has a protective effect in reducing unwanted side reactions in materials such as a blood product, while permitting pathogen inactivation to occur.

Definitions

"Pathogen" is defined as any nucleic acid containing agent capable of causing disease in a human, other mammals, or vertebrates. The pathogenic agent may be unicellular or multicellular. Examples of pathogens are bacteria, viruses, protozoa, fungi, yeasts, molds, and mycoplasmas which cause disease in humans, other mammals, or vertebrates. The genetic material of the pathogen may be DNA or RNA, and the genetic material may be present as single-stranded or double-stranded nucleic acid. Table I lists examples of viruses, and is not intended to limit the invention in any manner.

TABLE I

| Family: | Virus: |
| --- | --- |
| Adeno | Adenovirus 2 |
|  | Canine hepatitis |
| Arena | Pichinde |
|  | Lassa |
| Bunya | Turlock |
|  | California encephalitis |
| Herpes | Herpes simplex 1 |
|  | Herpes simplex 2 |
|  | Cytomegalovirus |
|  | Pseudorabies |
| Orothomyxo | Influenza |
| Papova | SV-40 |

TABLE I-continued

| Family: | Virus: |
| --- | --- |
| Paramyxo | Measles |
|  | Mumps |
|  | Parainfluenza 2 and 3 |
| Picorna | Poliovirus 1 and 2 |
|  | Coxsackie A-9 |
|  | Echo 11 |
| Pox | Vaccinia |
|  | Fowl Pox |
| Reo | Blue tongue |
|  | Colorado tick fever |
| Retro | HIV |
|  | Avian sarcoma |
|  | Murine sarcoma |
|  | Murine leukemia |
| Rhabdo | Vesicular stomatitis virus |
| Toga | Western equine encephalitis |
|  | Dengue 2 |
|  | Dengue 4 |
|  | St. Louis encephalitis |
| Hepadna | hepatitis B |
| Bacteriophage | Lambda |
|  | R17 |
|  | T2 |
| (Rickettsia) | R. akari (rickettsialpox) |

"In vivo" use of a material or compound is defined as introduction of the material or compound into a living human, mammal, or vertebrate.

"In vitro" use of a material or compound is defined as a use of the material or compound outside a living human, mammal, or vertebrate, where the material or compound is not intended for reintroduction into a living human, mammal, or vertebrate. An example of an in vitro use would be the analysis of components of a blood sample using laboratory equipment.

"Ex vivo" use of a compound is defined as using a compound for treatment of a biological material outside a living human, mammal, or vertebrate, where that treated biological material is intended for use inside a living human, mammal, or vertebrate. For example, removal of blood from a human, and introduction of a compound into that blood to inactivate pathogens, is defined as an ex vivo use of that compound if the blood is intended for reintroduction into that human or another human. Reintroduction of the human blood into that human or another human would be in vivo use of the blood, as opposed to the ex vivo use of the compound. If the compound is still present in the blood when it is reintroduced into the human, then the compound, in addition to its ex vivo use, is also introduced in vivo.

"Materials which may be treated" include any materials, including biological materials. Such materials include chemicals, solutions, including salt or buffered solutions, and solvents. Any materials that will come into contact with, or be introduced into, a living human, mammal, or vertebrate, where such contact carries a risk of transmitting disease or pathogens may be treated as disclosed herein.

"Biological material" is defined as a material originating from a biological organism of any type. Examples of biological materials include, but are not limited to, blood, blood products such as plasma, fractionated plasma, platelet preparations, red blood cells and packed red blood cells, cerebrospinal fluid, saliva, urine, sweat, feces, semen, milk, tissue samples, homogenized tissue samples, and any other substance having its origin in a biological organism. Biological materials also include synthetic material incorporating a substance having its origin in a biological organism, such as a vaccine preparation including a pathogen or portion thereof (the pathogen, in this case, being the substance having its origin in a biological organism) or a recombinant protein, a sample prepared for analysis which is a mixture of blood and analytical reagents, cell culture medium, cell cultures, viral cultures, and other cultures derived from a living organism.

"Inactivation of pathogens" is defined as rendering pathogens in a material incapable of reproducing. Inactivation is expressed as the negative logarithm of the fraction of remaining pathogens capable of reproducing. Thus, if a compound at a certain concentration renders 90% of the pathogens in a material incapable of reproduction, 10% or one-tenth (0.1) of the pathogens remain capable of reproduction. The negative logarithm of 0.1 is 1, and that concentration of that compound is said to have inactivated the pathogens present by 1 log. Alternatively, the compound is said to have 1 log kill at that concentration. Thus, if a compound at a certain concentration renders all but 10% or one tenth (0.1) of the pathogens incapable of reproduction, it is said to inactivate the pathogens by 1 log. Inactivating all but 1% or 0.1% of the pathogens would correspond to a 2 log or 3 log, respectively, reduction of pathogen at that concentration of the compound.

Compounds to be Quenched

A variety of compounds may be quenched in materials, such as biological materials, using the methods disclosed herein. Compounds that may be quenched include compounds that comprise a functional group which is, or which is capable of forming and has formed, e.g., in situ, a reactive group, such as an electrophilic group. For example, the functional group may be a mustard group that is capable of forming in situ a reactive group, such as an electrophilic aziridine, aziridinium, thiirane or thiiraniium ion. In another embodiment the functional group may be an epoxide. The quencher comprises a nucleophilic group and acts to trap electrophilic reactive groups on the compound by covalent reaction of the nucleophilic group on the quencher with the reactive electrophilic group. The quencher may be used to trap reactive species including the compound comprising an electrophilic group as well as reactive species formed therefrom.

In one embodiment, methods are provided for quenching compounds that are used to inactivate pathogens in materials. In blood products, pathogens which would be desirable to inactivate include microorganisms such as prokaryotic, eukaryotic and viral microorganisms containing nucleic acids, as well as nucleic acid genomes or fragments thereof from such microorganisms. Examples of viruses which can be inactivated include lipid coated viruses such as vesicular stomatitis virus (VSV), Moloney sarcoma virus, Sindbis virus, human immunodeficiency viruses (HIV-1, HIV-2), human T-cell lymphotorophic virus-I (HTLV-I), hepatitis-B virus, hepatitis C and herpes group viruses, as well as non-enveloped viruses including parvovirus.

Compounds have been developed which are used to inactivate pathogens in biological materials, wherein the compounds include, or react in situ to form, reactive electrophilic groups, without requiring photoactivation. The reactive electrophilic groups react with the nucleic acids of pathogens such as viruses, and bacteria to inactivate them. These reactive compounds, however, also may participate in unwanted side reactions. Provided herein are methods of adding quenching compounds to reduce unwanted side reactions of these compounds, which inactivate pathogens by reaction of electrophilic groups on the compound with the pathogen.

Examples of pathogen inactivating compounds which form reactive electrophilic groups and may be used to inactivate pathogens are described in PCT WO 96/14737, PCT WO 96/39818 and in U.S. Provisional Application Ser. No. 60/043,696, filed Apr. 15, 1997, the disclosures of which are incorporated herein. Additionally, nitrogen mustard, $C_3-N(CH_2CH_2Cl)_2$ may inactivate certain pathogens. LoGrippo el al., Proceedings of the Sixth Congress of the International Society of Blood Transfusion, Bibliotheca Haematologica (Hollander, ed.), 1958, pp. 225–230.

Preferred are pathogen inactivating compounds which include an anchor covalently bonded to an effector. The term "anchor" refers to a moiety which is capable of binding non-covalently to a nucleic acid biopolymer, such as DNA or RNA. The "anchor" is also referred to as a "nucleic acid binding ligand". The term "effector" refers to a moiety which is capable of reacting with a nucleic acid to form a covalent bond with the nucleic acid. Preferably, the effector is a functional group which is, or which is capable of forming an electrophilic group, wherein the electrophilic group is capable of forming a covalent bond with a nucleic acid. For example, PCT WO 96/14737, PCT WO 96/39818, and U.S. Pat. No. 5,559,250, the disclosures of which are incorporated herein, describe pathogen inactivating compounds which include an effector which is a mustard group, and a nucleic acid binding ligand. Pathogen inactivating compounds which include an aziridine covalently attached to a polyamine anchor also may be used, as described in Budowsky et al., Vaccine Research 5: 29–39 (1996); and PCT WO 97/07674, the disclosures of which are incorporated herein by reference.

An exemplary compound is quinacrine mustard, the structure of which is shown below.

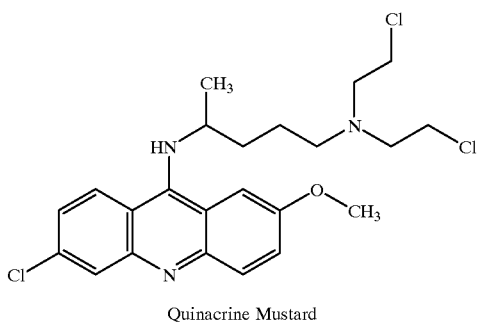

Quinacrine Mustard

The pathogen inactivating compounds also may be provided in a form wherein the anchor is covalently bonded to a frangible linker, which is covalently bonded to the effector. The term "frangible linker" refers to a moiety which covalently links the anchor and effector, and which is capable of degrading under certain conditions so that the anchor and effector are no longer linked covalently. The anchor-frangible linker-effector arrangement enables the compounds to bind specifically to nucleic acid, due to the anchor's binding ability. This brings the effector into proximity for reaction with the nucleic acid. Pathogen inactivating compounds including an anchor-frangible linker-effector arrangement are disclosed in U.S. Provisional Application Ser. No. 60/043,696, filed Apr. 15, 1997 and in U.S. patent application Ser. No. 09/003,115, filed Jan. 6, 1998, now U.S. Pat. No. 6,093,725, the disclosures of which are incorporated herein by reference. The effector can be, for example, a mustard group, mustard group equivalent, or epoxide.

Exemplary pathogen inactivating compounds (PIC) include PIC-1 and PIC-2, the structures of which are shown below. PIC-1 includes a frangible linker, with an ester functionality, while PIC-2 includes a frangible linker, with an amide functionality.

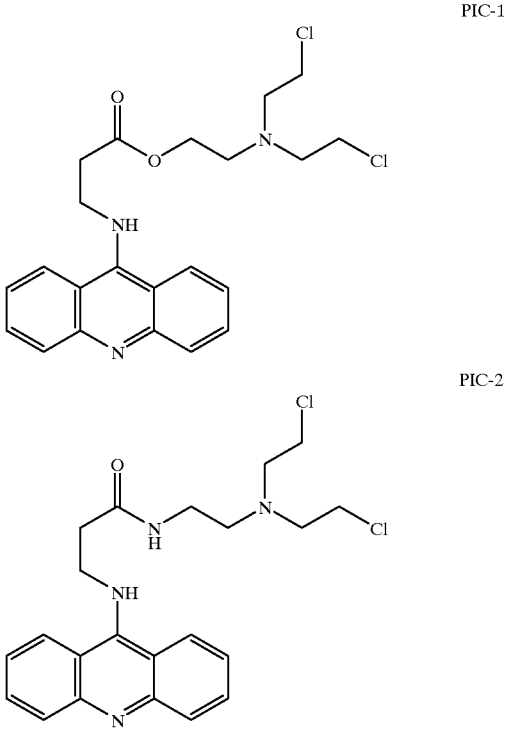

A wide variety of groups are possible for use as the anchors, linkers, and effectors. Examples of anchor groups include, but are not limited to, intercalators, minor groove binders, major groove binders, molecules which bind by electrostatic interactions, including polyamines, and molecules which bind by sequence specific interactions. The following is a non-limiting list of possible anchor groups:

acridines (and acridine derivatives, e.g. proflavine, acriflavine, diacridines, acridones, benzacridines, quinacrines), actinomycins, anthracyclinones, rhodomycins, daunomycin, thioxanthenones (and thioxanthenone derivatives, e.g. miracil D), anthramycin, mitomycins, echinomycin (quinomycin A), triostins, ellipticine (and dimers, trimers and analogs thereof), norphilin A, fluorenes (and derivatives, e.g. flourenones, fluorenodiamines), phenazines, phenanthridines, phenothiazines (e.g., chlorpromazine), phenoxazines, benzothiazoles, xanthenes and thioxanthenes, anthraquinones, anthrapyrazoles, benzothiopyranoindoles, 3,4-benzopyrene, 1-pyrenyloxirane, benzanthracenes, benzodipyrones, quinolines (e.g., chloroquine, quinine, phenylquinoline carboxamides), furocoumarins (e.g., psoralens and isopsoralens), ethidium, propidium, coralyne, and polycyclic aromatic hydrocarbons and their oxirane derivatives;

distamycin, netropsin, other lexitropsins, Hoechst 33258 and other Hoechst dyes, DAPI (4',6-diamidino-2-phenylindole), berenil, and triarylmethane dyes;

aflatoxins;

spermine, spermidine, and other polyamines; and nucleic acids or analogs which bind by sequence specific interactions such as triple helix formation, D-loop formation, and direct base pairing to single stranded targets. Derivatives of these compounds are also non-limiting examples of anchor groups, where a derivative of a compound includes, but is not limited to, a compound which bears one or more substituent of any type at any location, oxidation or reduction products of the compound, etc.

Examples of frangible linkers include, but are not limited to, moieties that include functional groups such as ester (where the carbonyl carbon of the ester is between the anchor and the $sp^3$ oxygen of the ester; this arrangement is also called "forward ester"), "reverse ester" (where the $sp^3$ oxygen of the ester is between the anchor and the carbonyl carbon of the ester), thioester (where the carbonyl carbon of the thioester is between the anchor and the sulfur of the thioester, also called "forward thioester"), reverse thioester (where the sulfur of the thioester is between the anchor and the carbonyl carbon of the thioester, also called "reverse thioester"), forward and reverse thionoester, forward and reverse dithioic acid, sulfate, forward and reverse sulfonates, phosphate, and forward and reverse phosphonate groups. "Thioester" designates the —C(=O)—S— group; "thionoester" designates the —C(=S)—O— group, and "dithioic acid" designates the —C(=S)—S— group. The frangible linker also may include an amide, where the carbonyl carbon of the amide is between the anchor and the nitrogen of the amide (also called a "forward amide"), or where the nitrogen of the amide is between the anchor and the carbonyl carbon of the amide (also called a "reverse amide"). For groups which can be designated as "forward" and "reverse", the forward orientation is that orientation of the functional groups wherein, after hydrolysis of the functional group, the resulting acidic function is covalently linked to the anchor moiety and the resulting alcohol, thiol or amine function is covalently linked to the effector moiety. The reverse orientation is that orientation of the functional groups wherein, after hydrolysis of the functional group, the resulting acidic function is covalently linked to the effector moiety and the resulting alcohol or thiol function is covalently linked to the anchor moiety.

The frangible linker, such as an amide moiety, also may be capable of degrading under conditions of enzymatic degradation, by endogenous enzymes in the biological material being treated, or by enzymes added to the material.

Examples of effectors include, but are not limited to, mustard groups, mustard group equivalents, epoxides, aldehydes, formaldehyde synthons, and other alkylating and cross-linking agents. Mustard groups are defined as including mono or bis haloethylamine groups, and mono haloethylsulfide groups. Mustard group equivalents are defined by groups that react by a mechanism similar to the mustards, such as mono or bis mesylethylamine groups, mono mesylethylsulfide groups, mono or bis tosylethylamine groups, and mono tosylethylsulfide groups. Formaldehyde synthons are defined as any compound that breaks down to formaldehyde in aqueous solution, including hydroxymethylamines such as hydroxymethylglycine. Examples of formaldehyde synthons are given in U.S. Pat. No. 4,337,269 and in International Patent Application WO 97/02028.

The concentration of the pathogen inactivating compound may be selected based on factors such as types of pathogens, the nature of the biological material treated, and the inactivating compound used.

Quenching Compounds

Methods are provided for the treatment of biological materials with quenching compounds, also referred to herein as "quenchers", to reduce unwanted side reactions of reactive electrophilic species in the material. In particular, methods are provided for quenching undesired side reactions of pathogen inactivating compounds that inactivate pathogens in biological materials, wherein the pathogen inactivating compounds either contain or are capable of forming electrophilic groups which damage the nucleic acid of pathogens. The quencher reduces unwanted reactions of the pathogen inactivating compound and of reaction products produced by the pathogen inactivating compound. Preferred are quenchers that include nucleophilic groups capable of reacting with the electrophilic groups on the pathogen inactivating compound. The quencher comprising a nucleophilic group acts to trap reactive electrophilic groups on the compound by covalent reaction of the nucleophilic group on the quencher with the reactive electrophilic group. Reactive species that may be trapped by the quencher include the compound comprising an electrophilic group as well as species comprising a reactive electrophilic group formed therefrom.

An advantage of the methods disclosed herein is that an effective amount of the quencher may be used such that unwanted side reactions of the pathogen inactivating compound are reduced, however, pathogen inactivation by the pathogen inactivating compound can still occur. The quencher thus has a protective effect in reducing unwanted side reactions in materials such as blood, while permitting pathogen inactivation to occur. A variety of side reactions can be reduced. For example, in methods where materials containing blood products are treated, modification of red blood cells may be reduced. For example, the binding of proteins, such as IgG, and/or the binding of the pathogen inactivating compound to red blood cells may be reduced.

In one embodiment, a biological material, such as a blood product, is treated with a pathogen inactivating compound comprising a functional group which is, or which is capable of forming, an electrophilic group and the quencher. In a preferred embodiment, the pathogen inactivating compound includes a nucleic acid binding ligand and an effector that is a functional group which is, or which is capable of forming, a reactive electrophilic group. The electrophilic group may be, for example, an oxirane, thiirane, thiiranium, or aziridinium ion or aziridine. The effector may be a mustard group which is capable of forming the electrophilic group. The mustard group can, for example, be capable of forming an electrophilic aziridine, or an electrophilic aziridinium or thiiranium ion, in situ.

In the method, the biological material is treated with a quencher comprising a nucleophilic functional group that is capable of covalently reacting with the electrophilic group on the pathogen inactivating compound. The quencher is added to the material prior to, simultaneously with, or after the addition of the pathogen inactivating compound. In a preferred embodiment, the quencher is added prior to or simultaneously with addition of the pathogen inactivating compound. In one particularly preferred embodiment, the quencher is added simultaneously with the pathogen inactivating compound. In another preferred embodiment, the quencher is added within about 30 minutes, for example, within about 15–20 minutes, or optionally, within about 10 minutes before or after addition of the pathogen inactivating compound. The material may be treated, for example, in vitro or ex vivo. Preferred are quenchers which reduce unwanted side reactions of the pathogen inactivating compounds without interfering with the ability of the pathogen inactivating compound to inactivate pathogens, and without substantially changing the properties of the biological material.

Examples of quenchers are compounds including nucleophilic groups, or other groups that react with electrophilic groups. Mixtures of quenching compounds also may be used. Exemplary nucleophilic groups include thiol, thioacid, dithioic acid, thiocarbamate, dithiocarbamate, amine, phosphate, and thiophosphate groups. The quencher may be, or contain, a nitrogen heterocycle such as pyridine. The quencher can be a phosphate containing compound such as glucose-6-phosphate. The quencher also can be a thiol containing compound, including, but not limited to, glutathione, cysteine, N-acetylcysteine, mercaptoethanol, dimercaprol, mercaptan, mercaptoethanesulfonic acid and salts thereof, e.g., MESNA, homocysteine, aminoethane thiol, dimethylaminoethane thiol, dithiothreitol, and other thiol containing compounds. The quenchers also can be in the form of a salt, such as sodium or hydrochloride salt.

Other thiol containing compounds include methyl thioglycolate, thiolactic acid, thiophenol, 2-mercaptopyridine, 3-mercapto-2-butanol, 2-mercaptobenzothiazole, thiosalicylic acid and thioctic acid. Exemplary aromatic thiol compounds include 2-mercaptobenzimidazolesuffonic acid, 2-mercapto-nicotinic acid, napthalenethiol, quinoline thiol, 4-nitro-thiophenol, and thiophenol. Other quenchers include nitrobenzylpyridine and inorganic nucleophiles such as selenide salts or organoselenides such as selenocysteine, thiosulfate, sulfite, sulfide, thiophosphate, pyrophosphate, hydrosulfide, and dithionite. The quencher also can be a peptide compound containing a nucleophilic group. For example, the quencher may be a cysteine containing compound, for example, a dipeptide, such as GlyCys, or a tripeptide, such as glutathione.

Also within the scope of the invention are macromolecular complexes which include the nucleophilic group or a compound containing the nucleophilic group. In another embodiment, the nucleophilic group, such as a thiol group, or compound including the nucleophilic group, is immobilized on a solid support, such as a chromatography material, to form an immobilized quencher. The solid support may be, for example an agarose, polystyrene or other chromatography material. For example, glutathione, or other compounds containing a nucleophilic group such as a sulfur group, may be attached to epoxy activated agarose. For example, glutathione-agarose, is commercially available from Sigma (St. Louis, Mo.), wherein glutathione is attached through the amino group to epoxy activated 4% cross-linked beaded agarose via a 10 carbon spacer. Additionally, cysteine-agarose is available from Sigma which is attached through the amino group to cyanogen bromide activated 4% cross-linked beaded agarose. Any of a range of activated chromatography resins or other materials can be derivatized to include one, two, or more nucleophilic groups. Such activated matrices that can be derivatized include cyanogen bromide, epoxy, nitrophenyl and N-hydroxysuccinimidyl chloroformate, thio pyridyl, polyacrylhydrazido, and oxirane acrylic activated matrices. Other exemplary chromatography materials including immobilized nucleophilic groups, such as thiols, which are commercially available include Duolite GT-73 polystyrene thiol containing resin and Duolite C-467 which includes amino phosphonic group (Supelco, Bellefonte, Pa.).

In another embodiment, the reaction of the quencher can be catalyzed by reaction of an enzyme, such as glutathione transferase. The presence of glutathione transferase can also influence the reactivity of the quencher with the pathogen inactivating compound comprising an electrophilic group. For example, glutathione transferase may be compartmentalized in a membrane system, to allow quenching to occur and be enhanced in the area where the glutathione transferase is present.

The quencher also may be generated by in situ, for example, by reaction of an enzyme, or through a chemical rearrangement from a precursor molecule. An example of a compound that generates a quencher in situ by enzymatic catalysis is amifostene (Ethyol(®), U.S. Bioscience, West Conshohocken, Pa.).

Preferred Properties of Quenchers for the Treatment of Blood Products In one embodiment, methods are provided for quenching undesired side reactions of a pathogen inactivating compound in a biological material comprising red blood cells. For example, the material may be a blood product with a hematocrit of about 30–85%. The pathogen inactivating compound preferably includes a functional group which is, or which is capable of forming, an electrophilic group.

The quencher is added to the blood product prior to, simultaneously with, or after the addition of the pathogen inactivating compound. Preferably, in the treatment of a blood product, the quencher is added prior to or contemporaneously with the pathogen inactivating compound. In another preferred embodiment, the quencher is added within about 30 minutes, or within about 15–20 minutes, or optionally, within about 10 minutes of addition of the pathogen inactivating compound. Examples of blood products which may be treated include whole blood, platelets, red blood cells and plasma. Preferred quenchers are compounds which reduce the unwanted side reactions of the reactive compounds, without significantly affecting pathogen inactivation, or the blood product. For example, quenchers may be added to a blood product treated with a pathogen inactivating compound, wherein the pathogen inactivating compound includes i) a nucleic acid binding ligand, capable of non-covalently binding to a nucleic acid; and ii) a group which is, or which is capable of forming an electrophilic group, such as a cationic electrophilic group. Preferred are quenchers which can reduce unwanted side reactions of the compounds without significantly affecting pathogen inactivation or the properties of the particular blood product being treated. One preferred quencher is glutathione.

The pathogen inactivating compound in a preferred embodiment includes a nucleic acid binding ligand and a mustard group that is capable of reacting in situ to form the electrophilic group, wherein the electrophilic group is an aziridinium ion. Compounds including a non-covalent nucleic acid binding ligand and a mustard group are described, for example, in U.S. Pat. No. 5,559,250. Exemplary compounds include quinacrine mustard. These compounds are believed to inactivate pathogens by binding to and alkylating their nucleic acid material. In the inactivation reaction, the mustard group on the compound forms a reactive aziridinium ion. The nucleic acids of pathogens are believed to react with the compounds by nucleophilic attack of the nucleic acid on the electrophilic aziridinium intermediate formed by the compound. While not being limited to any theory, it is believed that quenchers such as glutathione react with these pathogen inactivating compounds in a similar manner, by nucleophilic attack of the quencher on the electrophilic aziridinium intermediate, to produce a reaction product or products that are no longer capable of reacting with nucleic acids.

While not being limited to any theory, a proposed mechanism of the reaction of nucleophiles ($Nu_1$ and $Nu_2$) with a mustard group on a pathogen inactivating compound is shown in Scheme 1 below.

Scheme 1

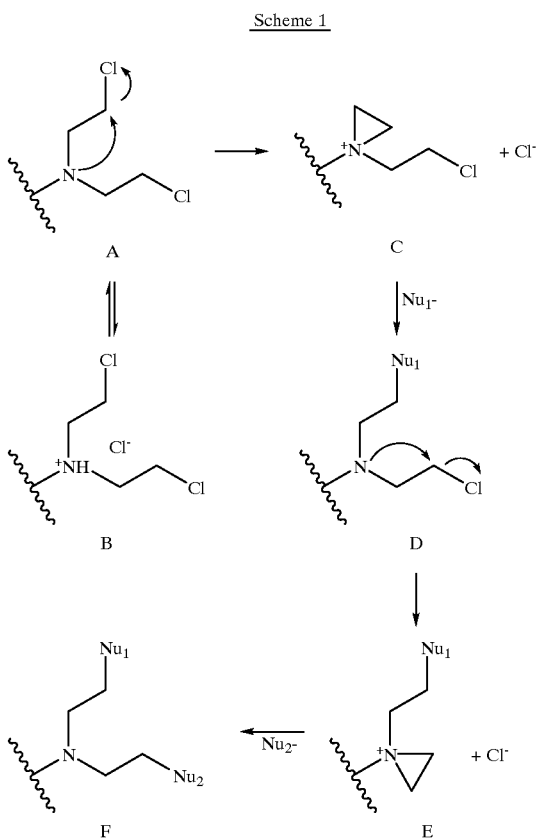

The mustard group can be in either the protonated form B, or in the deprotonated form A, as shown in Scheme I. Typically at physiological pH, the intramolecular formation of the aziridinium intermediates C and E is facile. Quenchers including nucleophilic groups are used which are capable of reacting with the aziridinium intermediates C and E, to form the final product F, wherein the nucleophilic groups have replaced the chlorine atoms of the mustard group.

Although the reactivity of the aziridinium ion is high, reaction rates are still dependent upon the properties of the reacting nucleophile. Furthermore, the quencher nucleophiles can compete with other endogenous nucleophiles present, for example when present at a higher concentration than the other endogenous nucleophiles, or when they are more reactive. Under physiological conditions, the preferred nucleophilic group is a thiol group. Other nucleophilic groups include phosphates and amino groups.

The quencher preferably maintains the blood product function and minimizes side effects of the pathogen inactivating compound. A preferred quencher for the treatment of blood products, particularly blood products containing red blood cells, is glutathione. Glutathione is particularly useful for use in the treatment of red blood cell containing materials in combination with pathogen inactivation agents which form aziridinium intermediates, such as pathogen inactivating compounds containing mustard groups. The thiol group of glutathione reacts faster with the aziridinium intermediate than with the parent mustard compound.

The quencher preferably substantially does not penetrate external pathogen membranes, such as cell membranes and viral lipid coats. The quencher preferably does not penetrate the lipid membranes of viruses, bacteria and other target pathogens to such a degree that it significantly decreases the damage caused by the pathogen inactivating compound, to the nucleic acid of the pathogen. Additionally, the quencher preferably reacts with the electrophilic group formed from the pathogen inactivating compound, in preference to reacting with the compound itself. While not being limited to any theory, it is believed that, the pathogen inactivating compound can freely cross pathogen membranes, such as viral lipid coats and bacterial membranes, but after the cationic electrophilic group, such as an aziridinium ion, is formed, the compound cannot cross pathogen membranes to any significant extent. Thus, electrophilic cations which form outside the target pathogen substantially cannot crosslink nucleic acid; the quencher can, however, react with them. Conversely, if the electrophilic cation forms inside the pathogen, in one embodiment, the quencher is inefficient in traversing the pathogen membrane, and nucleic acid crosslinking proceeds without substantially significant interference from the added quencher.

It is preferred that the quencher react with the pathogen inactivating compound to quench unwanted side reactions without interfering with pathogen inactivation by the pathogen inactivating compound. This may occur, for example, by the use of a quencher which substantially does not traverse pathogen membranes, and therefore quenches side reactions outside the pathogen membranes. In another embodiment, the quencher may react kinetically so slowly with the pathogen inactivating compound, or reactive intermediates formed therefrom, that it substantially does not interfere with pathogen inactivation.

In one embodiment, quenchers may be administered to multiphase systems, such as two phase systems comprising a membrane that separates the first and second phases. In one embodiment, in the two phase system, one phase is bounded by a membrane. The membrane may be a natural or artificial semi-permeable barrier composed of natural or synthetic molecules or mixtures thereof. For example, the membrane bounded phase may be the interior of a pathogenic organism, and the other phase may be the phase in which the pathogenic organism is contained. For example, the pathogen may be suspended in a fluid phase, such as a liquid phase including blood. The membrane bounded phase, e.g., may be the interior of a viral lipid coat comprising viral nucleic acids. In another embodiment, the membrane may be a cell membrane, and the membrane bounded phase may be the interior of a pathogenic unicellular organism, such as a bacteria. At least a portion of the pathogen inactivating compound preferably is kinetically or thermodynamically capable of traversing the membrane, while the quencher is substantially kinetically or thermodynamically not capable of traversing the membrane, relative to the pathogen inactivating compound.

Other membranes include liposomes, as described, for example, in Lasic, D., *Liposomes in Gene Delivery*, CRC Press, Boca Raton, Fla., 1997, Chapter 6. The liposomes may be formed as vesicular particles using self-assembled amphiphilic molecules, such as lecithins, sphingomyelins, and phosphatidylethanolamines. Liposomes also may be formed using negatively charged lipids such as phosphatidylserines, phosphatidylglycerols and phosphatidylinositols. Cationic liposomes also may be prepared using cationic detergents that are commercially available, or using polycationic groups linked to cholesterol, as described in Gao and Huang, *Biochem. Biophys. Res. Commun.*, 179: 280–285 (1991); *Nucleic Acids Res.*, 21: 2867–2872 (1993); and *Biochemistry*, 35: 1027–1036 (1996). Membranes also include artificial viral envelopes, as described in U.S. Pat. No. 5,753,258, the disclosure of which is incorporated herein. Membranes further include the membranes of non-pathogenic cells such as leucocytes.

In one embodiment, a method is provided for quenching undesired side reactions of a pathogen inactivating compound in a two phase biological material comprising a first phase comprising a liquid having a pathogen comprising a membrane therein, and a second phase bounded by the membrane of the pathogen. The biological material is treated with a pathogen inactivating compound comprising a functional group which is capable of forming an electrophilic group. Prior to, contemporaneously, or after treatment with the pathogen inactivating compound, the biological material is treated with a quencher comprising a nucleophilic group that is capable of covalently reacting with the electrophilic group. Preferably, the quencher is added prior to or contemporaneously with the pathogen inactivating compound. In another preferred embodiment, the quencher is added within about 30 minutes, or within about 15–20 minutes, or optionally within about 10 minutes before or after addition of the pathogen inactivating compound.

Preferably, the pathogen inactivating compound substantially kinetically traverses the membrane, prior to formation of the electrophilic group, relative to the quencher. The pathogen inactivating compound also preferably substantially kinetically does not traverse the membrane after formation of the electrophilic group, relative to the pathogen inactivating compound prior to the formation of the electrophilic group. The quencher is permitted to react with the electrophilic group of the pathogen inactivating compound, and the reaction of the quencher with the electrophilic group of the pathogen inactivating compound occurs substantially in the first phase. The pathogen inactivating compound comprising the electrophilic group reacts with a nucleic acid of the pathogen in the second phase, within the pathogen membrane, thereby to inactivate the pathogen. The membrane, may comprise, for example, a lipid. The pathogen may be, for example, a virus comprising a lipid coat defining the membrane, wherein the second phase is defined by the interior of the lipid coat. The pathogen also may be a bacteria comprising a cell membrane comprising a lipid defining the membrane of the two phase system, wherein the second phase is defined by the interior of the cell membrane.

Advantageously, in the two phase system, the quencher is administered to the first phase and substantially is not capable of traversing the membrane of the pathogen. The pathogen inactivating compound is administered, for example, to the first phase. The pathogen inactivating compound is capable of traversing the membrane to the second phase, prior to formation of the electrophilic group. Upon formation of the electrophilic group in situ, the pathogen inactivating compound substantially is no longer capable of traversing the membrane. Thus, quenching selectively occurs in the first phase, while in the second phase, i.e., the interior of the pathogen, the pathogen inactivating compound reacts with nucleic acids of the pathogen without quenching. Thus, in a biological material, such as a blood product, quenching of reactive groups on the pathogen inactivating compound and degradation products thereof occurs selectively in the first phase in which the pathogen is suspended. The quenching in the first phase thus reduces unwanted side reactions of the reactive group on the pathogen inactivating compound in the first phase, such as covalent modification of proteins in blood. In the method, the pathogen inactivating compound and the quencher are administered in an effective amount to inactivate pathogens in the material while quenching undesired side reactions of the pathogen inactivating compound. The quencher thus has a protective effect in reducing unwanted side reactions in materials such as a blood product, while permitting pathogen inactivation to occur.

Glutathione has many properties that make it particularly useful as a quencher. It is normally present in all cell types. It is not believed substantially to be passively able to pass through the membranes, such as cell membranes or lipid coats, of bacteria and lipid-enveloped viruses. At pH 7, glutathione is charged and in the absence of active transport does not penetrate lipid bilayers to any significant extent. This is consistent with viral inactivation of VSV and other enveloped viruses being substantially unaffected by glutathione. Inactivation of lipid enveloped viruses such as HIV and VSV is not effected by the presence of glutathione or N-acetylcysteine, two thiol quenching agents. Glutathione has little effect on viral inactivation, and while it has some effect on inactivation of *Staphylococcus epidermis* and *Yersinia enterocolitica,* this can be managed by minimizing the dose of added quencher. For example, the presence of about 2–4 mM glutathione reduces inactivation by 0.3 mM PIC-1 of Yersinia enterocolitica by about 1 to 2 log kill. Glutathione is also compatible with in vitro storage of red blood cells.

Preferred are quenchers which substantially do not damage red blood cell function or modify red blood cells after treatment, and also substantially do not reduce pathogen inactivation by the pathogen inactivating compound. The lack of a substantially damaging effect on red blood cell function may be measured by methods known in the art for testing red blood cell function. For example, the levels of indicators such as intracellular ATP (adenosine 5'-triphosphate), intracellular 2,3-DPG (2,3-diphosphoglycerol) or extracellular potassium may be measured, and compared to an untreated control. Additionally hemolysis, pH, hematocrit, hemoglobin, osmotic fragility, glucose consumption and lactate production may be measured.

Methods for determining ATP, 2,3-DPG, glucose, hemoglobin, hemolysis, and potassium are available in the art. See for example, Davey el al., *Transfusion,* 32: 525–528 (1992), the disclosure of which is incorporated herein. Methods for determining red blood cell function are also described in Greenwalt et al., *Vox Sang,* 58: 94–99 (1990); Hogman et al., *Vox Sang,* 65: 271–278 (1993); and Beutler et al., *Blood,* Vol. 59 (1982) the disclosures of which are incorporated herein by reference. Extracellular potassium levels may be measured using a Ciba Corning Model 614 $K^+/Na^+$Analyzer (Ciba Corning Diagnostics Corp., Medford, Mass.). The pH can be measured using a Ciba Corning Model 238 Blood Gas Analyzer (Ciba Corning Diagnostics Corp., Medford, Mass.).

In the method of treatment of red blood cells with a pathogen inactivating compound including a nucleic acid binding ligand and a mustard group, in the presence of the quencher, such as glutathione, preferably, in one embodiment, the level of extracellular potassium is not greater than 3 times, more preferably no more than 2 times the amount exhibited in the untreated control after 1 day.

Also, in one embodiment, preferred are quenchers that inhibit undesired modification of red blood cells during pathogen inactivation, such as lysis or other damage. Preferably, hemolysis of the treated red blood cells is less than 3% after 28 day storage, more preferably less than 2% after 42 day storage, and most preferably less than or equal to about 1% after 42 day storage at 4° C.

Preferred are quenchers that can reduce protein binding, such as IgG binding, to red blood cells and that can be used under conditions that do not substantially inhibit pathogen inactivation in comparison to a control conducted in the absence of a quencher. Also preferred are quenchers which inhibit the binding of pathogen inactivating compounds to red blood cell surfaces. An exemplary quencher is glutathione. Glutathione advantageously reduces potential modification of red blood cells by pathogen inactivating compounds.

Binding of species such as IgG, albumin, and IgM to red blood cells also may be measured using methods available in the art. In one embodiment, in a method of treatment of red blood cells with a pathogen inactivating compound including a nucleic acid binding ligand and an effector such as a mustard group, in the presence of a quencher, IgG binding to red blood cells can be reduced in comparison to IgG binding in the absence of quencher. IgG binding to red blood cells in the presence of a quencher, such as glutathione, and the pathogen inactivating compound preferably is less than about 75%, or preferably less than about 50% of the IgG binding in the absence of quencher.

Binding of molecules to red blood cells can be detected using antibodies, for example to acridine and IgG. Antibodies for use in assays can be obtained commercially, or can be made using methods available in the art, for example as described in Harlow and Lane, "Antibodies, a Laboratory Manual, Cold Spring Harbor Laboratory," 1988, the disclosure of which is incorporated herein. For example, anti-IgG is commercially available from Caltag, Burlingame, Calif.; Sigma Chemical Co., St. Louis, Mo. and Lampire Biological Laboratory, Pipersvelle, Pa.

Preferred are quenchers that reduce binding of the pathogen inactivating compound, or fragments thereof, to red blood cells. In the embodiment wherein a biological material containing red blood cells is treated with a pathogen inactivating compound including an effector such as a mustard group and a nucleic acid binding group, such as an acridine group, binding of the pathogen inactivating compound, or fragments thereof to red blood cells can be reduced. For example, binding of acridine derived from a pathogen inactivating compound, wherein the nucleic acid binding ligand is acridine, to red blood cells can be reduced in the presence of a quencher such as glutathione. In a preferred embodiment, acridine binding to red blood cells treated with a pathogen inactivating compound including an acridine group in the presence of the quencher is less than about 75%, or preferably less than about 50%, or, in another preferred embodiment, less than about 5% of acridine binding in the absence of the quencher.

In one embodiment, quenchers are provided which decrease the concentration of reactive electrophilic alkylating species after pathogen inactivation, for example by at least about 5%, or about 20%, or optionally about 50%, or more, within about 1 to 48 hours, for example about 24 hours. The presence of the reactive electrophilic species may be determined using methods available in the art, such as chromatographic methods including LC-MS (liquid chromatography-mass spectroscopy).

Also preferred in one embodiment are quenchers that reduce the inactivation of a pathogen by the pathogen inactivating compound by no greater than about 1 log, or no greater than about 2 logs, or optionally no greater than about 3 logs, or in another embodiment no greater than 4 logs, in comparison to a control pathogen inactivation conducted in the absence of the quencher. Preferably, the quencher reduces inactivation of a viral pathogen by the pathogen inactivating compound by no greater than about 1 log, or no greater than about 2 logs, or optionally no greater than about 3 logs, in comparison to a control pathogen inactivation conducted in the absence of the quencher. The concentration of the pathogen inactivating compound and the quencher may be adjusted to obtain the desired log kill, and to minimize the reduction of inactivation which may occur due to the presence of the quencher.

In one preferred embodiment, a method is provided, wherein the method comprises treating a red blood cell containing material with an effective amount of the pathogen inactivating compound and the quencher to inactivate at least 2 logs of a pathogen, and wherein red blood cell function is not substantially altered by the treatment. In another preferred embodiment, a method is provided wherein the method comprises treating the material with an effective amount of the pathogen inactivating compound and the quencher to inactivate at least 2 logs of a pathogen, and wherein hemolysis of the red blood cells is less than 3% after 28 days of storage after treatment.

Red blood cells treated with glutathione do not show a significant difference in red blood cell function compared to untreated controls. Glutathione itself does not contribute to any significant extent to red blood cell lysis or other damage as measured by in vivo or in vitro functional assays. Glutathione may reduce red blood cell lysis in the presence of pathogen inactivating compounds. Red blood cells may be treated with glutathione in vitro or ex vivo. Some compounds such as thiosulfate, MESNA and N-acetylcysteine are either less active or may modify red blood cells at concentrations effective for quenching.

Conditions for Pathogen Inactivation and Quenching

Conditions for treating biological materials with a pathogen inactivating compound and a quencher to reduce unwanted side reactions may be selected based on the selected material, the quencher and the inactivating compound. A variety of biological materials may be treated with a pathogen inactivating compound and a quencher, for example in vitro or ex vivo. Conditions are selected to produce pathogen inactivation while not substantially altering the biological material.

In a preferred embodiment, blood products are inactivated with a pathogen inactivating compound including a nucleic acid binding ligand and an effector such as a mustard group, wherein the mustard group is capable of forming a reactive electrophilic group in situ. The blood product is treated with a quencher to prevent unwanted side reactions of the pathogen inactivating compound without significantly affecting the properties of the blood product. The quencher may be added to the blood product before, after, or contemporaneously with the pathogen inactivating compound. Preferably, the quencher is added prior to or contemporaneously with the pathogen inactivating compound. In another preferred embodiment, the quencher is added within about 30 minutes, or within about 15 to 20 minutes or optionally within about 10 minutes, before or after addition of the pathogen inactivating compound. Red blood cell containing materials may be treated, for example, in vitro or ex vivo.

The concentration of the pathogen inactivating compound and the quenching agent in the blood product being treated may be adjusted as needed to produce the desired reduction of unwanted side reactions, while still protecting the property of the material, such as red blood cell function, and also achieving the desired log kill of pathogens.

The concentration of the quencher may be, in one non-limiting example, about 0.1 mM to about 30 mM, or about 0.5 mM to 30 mM. A non-limiting example of conditions suitable for treatment of red blood cells is about 0.1 mM to about 30 mM glutathione, e.g., about 0.5 mM to 20 mM, or about 2 mM to 4 mM glutathione, or in one embodiment, about 1 mM to 3 mM.

The molar ratio of quencher:pathogen inactivating compound, in one non-limiting embodiment, may range from about 100:1 to 1:1, for example about 50:1, or, for example. about 10:1. A non-limiting exemplary ratio of glutathione:pathogen inactivating compound which may be used for the treatment of red blood cells may be from about 100:1 to 1:1, for example about 50:1 to 1:1, or in another embodiment, about 10:1 to about 2:1. In one preferred embodiment, the molar ratio of glutathione:pathogen inactivating compound is about 10:1. For example, in the treatment of a composition comprising red blood cells, the molar concentration of glutathione is preferably about 5 to 20 times, e.g., about 10 times the molar concentration of the pathogen inactivating compound. The ratio of quencher to pathogen inactivating compound will vary depending upon the pathogen inactivating compound and quencher selected.

Typical concentrations of pathogen inactivating compound including a nucleic acid binding ligand and an effector such as a mustard group are on the order of about 0.1$\mu$M to 5 mM, for example about 50 to 500 $\mu$M. For example, a concentration of pathogen inactivating compound may be used which is sufficient to inactivate at least about one log, for example, at least about 3 to 6 logs, or optionally at least about 5 or 6 logs of pathogen in the sample. In one embodiment, preferred pathogen inactivating compounds are those that produce at least 1 log kill at a concentration of no greater than about 500 $\mu$M, more preferably at least 3 logs kill at no greater than 500 $\mu$M concentration. In another non-limiting example, the pathogen inactivating compound may have at least 1 log kill, and preferably at least 6 logs kill at a concentration of about 0.1 $\mu$M to about 3 mM. For example, a concentration of about 0.15 mM quinacrine mustard and about 3 mM glutathione may be used to inactivate greater than 2 logs of VSV and HIV in a red blood cell containing composition, while preserving red blood cell function.

In one preferred embodiment, a method is provided, wherein the method comprises treating a red blood cell containing material with an effective amount of the pathogen inactivating compound and the quencher to inactivate at least 2 logs of a pathogen, and wherein red blood cell function is not substantially altered by the treatment. In another preferred embodiment, a method is provided wherein the method comprises treating the material with an effective amount of the pathogen inactivating compound and the quencher to inactivate at least 2 logs of a pathogen, and wherein hemolysis of the red blood cells is less than 3% after 28 days of storage.

Incubation of blood products with the pathogen inactivating compound and the quencher can be conducted for example, for at least about 0.5 to 48 hours or more, for example, at least about 1 to 48 hours, or at least about 1 to 24 hours, or, for example, at least about 8 to 20 hours. In another embodiment, the incubation continues until further processing or use of the material.

The quencher may be added to the material, such as a blood product, prior to, contemporaneously with, or after the pathogen inactivating compound. Preferably, the quencher is added prior to or contemporaneously with the pathogen inactivating compound. In another preferred embodiment, the quencher is added within about 30 minutes, or within about 15 to 20 minutes before or after addition of the pathogen inactivating compound.

Some quenchers, such as glutathione, may oxidize or otherwise degrade or react over time. For example, when the quencher is a thiol containing compound, the quencher may oxidize to form disulfide dimers. It is preferred to add the quencher to the material at a time and concentration such that the quencher can quench the pathogen inactivating compound before it has substantially degraded or otherwise reacted in situ. For example, when the quencher is glutathione, in the embodiment where the glutathione is added prior to the pathogen inactivating compound, the glutathione is preferably added less than about 12 hours before the addition of the pathogen inactivating compound. In a preferred embodiment, the glutathione is added contemporaneously with the pathogen inactivating compound. In another embodiment, the glutathione is added within 30 minutes, or about 15 to 20 minutes, or optionally about 10 minutes after addition of the pathogen inactivating compound. The addition of glutathione close to time of addition of the pathogen inactivating compound is advantageous to minimize possible reduction of glutathione concentration, for example, by oxidation or peptidolysis, which may occur, for example in some biological materials, such as plasma.

For red blood cells, the incubation is typically conducted at a temperature of about 2° C. to 37° C., preferably about 18° C. to 25° C. For example, when the quencher is glutathione, red blood cells may be incubated with the pathogen inactivating compound and glutathione for about 12 hours at a temperature of about 22° C. For platelets, the temperature is preferably about 20 to 24° C. For plasma, the temperature may be about 0 to 60° C., typically about 0–24° C.

Biological Materials

A variety of biological materials may be treated with a pathogen inactivating compound and a quenching compound. Biological materials which can be treated with the quenching compounds include blood products such as whole blood, packed red blood cells, platelets and fresh or frozen plasma. Blood products further encompass plasma protein portion, antihemophilic factor (Factor VIII), Factor IX and Factor IX complex, fibrinogens, Factor XIII, prothrombin and thrombin, immunoglobulins (such as IgG, IgA, IgD, IgE and IgM and fragments thereof), albumin, interferon, and lymphokines. Also contemplated are synthetic blood products.

Other biological materials include vaccines, recombinant DNA produced proteins and oligopeptide ligands. Also encompassed are clinical samples such as urine, sweat, sputum, feces, spinal fluid. Further encompassed are synthetic blood or blood product storage media.

Reducing the Concentration of Compounds in Materials after Treatment

The concentration of the pathogen inactivating compound and/or the quencher in a biological material, such as a blood product, can be reduced after the treatment, for example by adsorption in a batch or flow removal process. Methods and devices which may be used are described in PCT US96/09846; U.S. patent application Ser. No. 08/779,830, filed Jan. 6, 1997; and in the co-filed application, U.S. patent application Ser. No. 09/003,113, filed Jan. 6, 1998, the disclosures of each of which are incorporated herein by reference in their entirety.

The invention will be further understood by reference to the following non-limiting examples.

Materials

The following materials were used in the following Examples.

While it is commercially available from Baxter Healthcare Corp., Deerfield, Ill., Adsol used in this and the following experiments was made by sterile filtering the following mixture: 22 g glucose, 9 g NaCl, 7.5 g mannitol, and 0.27 g adenine in 1 liter of distilled water.

Erythrosol was obtained from Baxter Healthcare Corp., Deerfield, Ill., or was made by combining sodium citrate dihydrate (7.82 g); sodium acid phosphate dihydrate (0.73 g); sodium phosphate dihydrate (3.03 g); adenine (0.22 g); mannitol (7.74 g); and glucose (9 g) in 1 liter of distilled water.

Quinacrine mustard was obtained from Aldrich Chemical Co., St. Louis, Mo. Glutathione and cysteine were obtained from Sigma, St. Louis, Mo. PIC-1 (β-alanine, N-(acridin-9-yl), 2-[bis(2-chloroethyl)amino]ethyl ester) was synthesized as described in U.S. Provisional Application Ser. No. 60/043,696, filed Apr. 15, 1997, now U.S. patent application Ser. No. 09/003,115, filed Jan. 6, 1998, the disclosure of which is incorporated herein. PIC-2 (β-alanine, N-(acridin-9-yl), 2-[bis(2-chloroethyl)amino]ethyl amide) was synthesized as described in U.S. patent application Ser. No. 09/003, 115, filed Jan. 6, 1998, the disclosure of which is incorporated herein.

Vesicular stomatitis virus (VSV) was obtained from ATCC American Type Cell Culture, Rockville, Md. (titer 8.8 log units).

Whole blood was obtained from the Sacramento Blood Center (Sacramento Calif.).

Packed red blood cells (PRBCS) were obtained from the Sacramento Blood Center, with a hematocrit (HCT) of about 55–65%, or were prepared using Adsol or Erythrosol as the additive solution as follows: within 20 hours of receipt, units of whole blood received from the Sacramento Blood Bank were centrifuged at 3800 rpm for 5 minutes and the plasma expressed into another container; the % hematocrit was measured by filling a capillary tube with the blood sample and spinning for 5 minutes; the volume taken up by the red cells was compared to a calibration curve; 94 mL of Adsol or Erythrosol were added; final hematocrit ranged from 50 to 60 percent depending on the treatment.

EXAMPLES

EXAMPLE 1

Reaction of Phosphate Ion with Pathogen Inactivating Compounds

The reactivity of phosphate ion with pathogen inactivating compounds was demonstrated. Reactivity was found to increase for higher pH values, at higher temperatures and for higher phosphate ion concentrations.

Upon incubation of 100 μM PIC-1 with 25 mM phosphate buffer of increasing pH values at room temperature (RT), a large increase of the rate of decomposition was observed. At pH 2.2 a $t_{1/2}$ of 450 minutes was observed compared to a $t_{1/2}$ of 25 minutes at pH≈6. Reaction of PIC-1 with phosphate ions produces at least two observable phosphate intermediates as determined by HPLC. The diphosphate ester of PIC-1 further hydrolyzes at the frangible ester. LC/MS analysis of the reaction mixture between the PIC-1 and phosphate ions was conducted. The species observed under the reaction conditions (pH=7, phosphate buffer) were the diphosphate ester, the monophosphate ester of the diol, and the phosphate ester of the chlorohydroxy compound.

Quinacrine mustard, which lacks a frangible linker group, also reacted with phosphate ions. The reaction of 100 μM quinacrine mustard with 50 mM phosphate at room temperature is slower than the same reaction at 37° C. with 130 mM phosphate (t1/2=10 minutes and 3.5 minutes respectively). This is demonstrated by both the slower production of the final product bis phosphoester and by the longer lifetime of the intermediate species.

The reaction of quinacrine mustard with glucose-6-phosphate also was facile at pH=7.8. New product species were observed by HPLC, consistent with at least one adduct being formed with glucose-6-phosphate.

EXAMPLE 2

Reaction of Thiol and Other Nucleophiles with Pathogen Inactivating Compounds

The reactivity of the thiol containing compound glutathione with pathogen inactivating compounds was studied. Reactivity was found to increase at higher pH values, at higher temperatures and for higher concentrations of thiol. 1 mM quinacrine mustard was incubated in 25 mM HEPES (N-[2-hydroxyethylpiperazine-N'-[2-ethanesulfonic acid], Sigma, St. Louis, Mo.), at pH 7 with 4 mM glutathione (GSH). Additionally, 100 μM PIC-1 was incubated in 25 mM HEPES at pH 7 with 4 mM GSH at room temperature. The reactions of quinacrine mustard and PIC-1 with glutathione occurred with a t1/2 of 50 minutes and 32 minutes, respectively. The PIC-1/GSH bis adduct was identified by mass spectroscopy. LC/MS analysis of the reaction mixture with glutathione at early time points identified the Olutathione monoadduct/aziridinium intermediate.

The reaction of the thiols with the pathogen inactivating compounds was also followed by monitoring the disappearance of the thiol groups, measured through the Ellman reaction, which was conducted as described in *Aldrichimica Acta*, 4: 33 (1971), the disclosure of which is incorporated herein. The Ellman reaction demonstrated the reaction of a compound containing two 2-chloroethyl groups (quinacrine mustard) with thiols in a 1:1.9 stoichiometry and a time course which is consistent with the decomposition of quinacrine mustard. These results demonstrate the quantitative reactivity of glutathione at the mustard center to form covalent thioether bonds.

Other thiols were found to react with PIC-1, including N-acetyl cysteine, cysteine, homocysteine, the dipeptide GlyCys, aminoethane thiol, dimethylaminoethane thiol, dithiothreitol, 2-mercaptonicotinic acid, 2-mercaptobenzimidazolesulfonic acid and quinoline thiol. The thiols are available commercially from Aldrich Chemical Company (St. Louis Mo.) or (Sigma, St. Louis, Mo.). In all cases the formation of intermediate species was observed through HPLC analysis of the reaction mixtures and consumption of the sulfhydryl group was observed through the Ellman reaction. Quinacrine mustard also was found to react with the nucleophiles, thiosulfate, hydrosulfide (HS⁻), and dithiocarbamate.

EXAMPLE 3

Study of Red Blood Cell Membrane Penetration of Glutathione

The ability of glutathione to penetrate red blood cell membranes was studied, as a model membrane system for the envelopes of viruses, since both would be devoid of any active transport systems for this peptide. The partitioning of the GSH inside and out of red cells (Sacramento Blood Center packed red blood cells, HCT 55–65%) was evaluated by determination of the amounts of thiol groups in the inside and the outside of the cells after addition of exogenous glutathione. Table 2 shows the total amount of glutathione (intracellular and supernatant) and the intracellular amount of glutathione of red blood cells as a function of time with and without addition of 3 mM GSH. The concentration of GSH was calculated based on the absorbance at 412 nm using a Beckman DU-20 (Beckman, Irvine, Calif.) single wavelength spectrometer. The results show that the amount of sulfhydryl groups in both compartments stays constant.

TABLE 2

| Time (min.) | Absorption 412 nm Total | GSH Concentration (mM) Total | Absorption 412 nm Supernatant | GSH Concentration (mM) Supernatant |
|---|---|---|---|---|
| 3mM Glutathione Added | | | | |
| 0 | 0.230 | 5.286 | 0.33 | 3.071 |
| 60 | 0.227 | 5.217 | 0.318 | 2.96 |
| 120 | 0.231 | 5.308 | 0.312 | 2.90 |
| 270 | 0.213 | 4.898 | 0.306 | 2.85 |
| 1080 | 0.227 | 5.217 | 0.297 | 2.77 |
| 1440 | 0.220 | 5.058 | 0.296 | 2.76 |
| No Glutathione Added | | | | |
| 0 | 0.082 | 1.914 | 0.001 | 0.028 |
| 60 | 0.082 | 1.914 | 0.001 | 0.028 |
| 120 | 0.086 | 2.005 | 0.001 | 0.028 |
| 270 | 0.075 | 1.754 | 0.002 | 0.037 |
| 1080 | 0.087 | 2.027 | 0.004 | 0.055 |
| 1440 | 0.084 | 1.959 | 0.003 | 0.046 |

EXAMPLE 4

Inactivation of Vesicular Stomatitis Virus with Quinacrine Mustard

The effect of various quenchers added 15 minutes following addition of a pathogen inactivator was studied. Vesicular stomatitis virus (VSV) (ATCC American Type Cell Culture, Rockville, Md., titer 8.8 log units/mL) was diluted into packed red blood cells (PRBCs), obtained from the Sacramento Blood Center, (Sacramento, Calif.), HCT 55–65%, and treated with 150 $\mu$M quinacrine mustard (QM). Fifteen minutes after the addition of QM, various quenchers were added at doses of between 1 to 10 mM. The quenchers were aminoethanethiol (AET), thiosulfate, glutathione and N-acetylcysteine (NAC), which were obtained from Aldrich Chemical Co. (St. Louis, Mo.). After a 4 hour room temperature inactivation, the viable virus was assayed in a viral plaque assay (Markus et al., Virology, 57: 321–338

Table 3 shows the results of inactivation of VSV by 150 $\mu$M QM in the presence of the various quenchers added after 15 minutes of incubation. In the absence of quencher, QM inactivated 3.5 logs of VSV. AET and thiosulfate decreased inactivation in a dose dependent manner. Neither glutathione nor NAC appeared to decrease VSV inactivation.

TABLE 3

| Sample | Concentration Quencher (mM) | Log Kill |
|---|---|---|
| QM only | none | 3.5 |
| QM + AET | 1 | 2.8 |
|  | 3 | 2.3 |
|  | 10 | 1.8 |
| QM + thiosulfate | 1 | 3.5 |
|  | 3 | 3.1 |
|  | 10 | 2.6 |
| QM + | 1 | 3.5 |

TABLE 3-continued

| Sample | Concentration Quencher (mM) | Log Kill |
|---|---|---|
| glutathione | | |
|  | 3 | 3.5 |
|  | 10 | 3.4 |
| QM + NAC | 1 | 3.6 |
|  | 3 | 3.8 |
|  | 10 | 3.8 |

EXAMPLE 5

Inactivation of Vesicular Stomatitis Virus with Quinacrine Mustard Added Simultaneously with Various Quenchers The effects of various quenchers added simultaneously with a pathogen inactivating compound were studied. Vesicular stomatitis virus (VSV) was diluted into packed red blood cells (PRBC). The PRBCs then were treated simultaneously with 150 $\mu$M quinacrine mustard (QM) and various quenchers added at doses of between 3 and 30 mM. The quenchers were aminoethanethiol (AET), thiosulfate, glutathione, N-acetylcysteine (NAC), cysteine and mercaptoethanesulfonic acid sodium salt (MESNA), obtained from Aldrich Chemical Co. (St. Louis, Mo.). After a 4 hour room temperature inactivation, the viable virus was assayed in a CPE assay (Baxt et al., Virology, 72: 383–392 (1976)) by evaluating the cytopathic effect (CPE) of the virus on baby hamster kidney (BHK) cells.

Table 4 illustrates the results of experiments where inactivation of VSV by 150 $\mu$M QM was conducted with simultaneous addition of AET, thiosulfate, glutathione or NAC. In this experiment, VSV was killed to below the limit of detection, >4.0 logs inactivated. Thus, certain quenchers may have had an effect of viral inactivation which was masked by this limit. AET and thiosulfate again showed significant inhibition of viral inactivation, with AET being the more potent inhibitor. Glutathione and NAC showed no evidence of effecting viral kill at concentrations of up to 10 mM, with some evidence of inhibition at 30 mM.

TABLE 4

| Sample | Concentration Quencher (mM) | Log Kill |
|---|---|---|
| QM only | none | >4.0 |
| QM + AET | 3 | 1.67 |
|  | 10 | 1.5 |
|  | 30 | 1.0 |
| QM + thiosulfate | 3 | 3.5 |
|  | 10 | 3.3 |
|  | 30 | 2.7 |
| QM + glutathione | 3 | >4.0 |
|  | 10 | >4.0 |
|  | 30 | 3.7 |
| QM + NAC | 3 | >4.0 |
|  | 10 | >4.0 |
|  | 30 | 4.0 |

Table 5 illustrates the results of another set of experiments where inactivation of VSV by 150 $\mu$M QM was conducted with simultaneous addition of glutathione, cysteine or MESNA. Inactivation by QM alone was 3.0 logs, and this level was not affected by glutathione even at 30 mM. Cysteine showed a dose-dependent decrease in viral inactivation, and MESNA gave mixed results with 2.3 logs kill at 30 mM quencher.

TABLE 5

| Sample | Concentration Quencher (mM) | Log Kill |
|---|---|---|
| QM only | none | 3.0 |
| QM + glutathione | 3 | 3.3 |
|  | 10 | 3.3 |
|  | 30 | 3.5 |
| QM + cysteine | 3 | 3.0 |
|  | 10 | 2.0 |
|  | 30 | 1.7 |
| QM + MESNA | 3 | 3.0 |
|  | 10 | 3.3 |
|  | 30 | 2.3 |

EXAMPLE 6

Inactivation of HIV using a Pathogen Inactivator and a Quencher

The effects of glutathione on inactivation of HIV by a pathogen inactivator in PRBCs was examined. PRBCs were prepared at a hematocrit of approximately 60% in Adsol additive solution. A stock of cell-free HIV-III$_B$ (Popovic et al., Science, 224: 497 (1984), approximately 8 logs/mL) was added to a titer of approximately 7 logs per mL.

To aliquots of HIV contaminated blood, glutathione was added to varying final concentration followed by addition of 50 μM PIC-1. Samples were incubated for 12 hours at room temperature. Red cells were then pelleted and residual virus in the supernatant fraction was detected using a microplaque assay (Hanson et al,. J. Clin. Microbio., 28: 2030 (1990)). Control samples were incubated with glutathione only to determine its effect on HIV viability.

The results of inactivation of HIV by PIC-1 and glutathione are shown in Table 6. The data in Table 6 demonstrate that inactivation of cell-free HIV was not inhibited by glutathione. There was some loss in HIV infectivity, approximately 0.2 logs, due to the incubation at room temperature for 12 hours (sample 1 vs. sample 3). 30 mM glutathione alone appeared to reduce the infectivity by another 0.3 to 0.6 logs (samples 2 and 4 compared to samples 1 and 3). With 50 μM PIC-1 only, inactivation was about 1.8 logs; 50 μM PIC-1 plus 30 mM glutathione inactivated about 2.4 logs. The apparent increase in inactivation can be accounted for entirely by the effect of glutathione itself. Over the range of 0.1 mM to 30 mM glutathione, there was a small increase in HIV inactivation which was consistent with the effects of glutathione only on HIV.

TABLE 6

| Sample # | PIC-1 (μM) | GSH (mM) | Log Titer | Log Kill |
|---|---|---|---|---|
| Incubation Controls (samples 1 and 2 = no incubation; 3 and 4 = 12 hour incubation) | | | | |
| 1 | none | none | 7.2 | — |
| 2 | none | 30 | 6.9 | 0.3 |
| 3 | none | none | 7.0 | — |
| 4 | none | 30 | 6.4 | 0.6 |
| PIC-1 Treated Samples (12 hour Incubation) | | | | |
| 5 | 50 | 0 | 5.2 | 1.8 |
| 6 | 50 | 0.1 | 5.2 | 1.8 |
| 7 | 50 | 0.3 | 5.2 | 1.8 |
| 8 | 50 | 1.0 | 5.0 | 2.0 |
| 9 | 50 | 3.0 | 5.0 | 2.0 |
| 10 | 50 | 10 | 4.7 | 2.3 |
| 11 | 50 | 30 | 4.6 | 2.4 |

Example 7

Treatment of Bacterially Contaminated RBCs with an Inactivator and a Quencher

The effects of the quenchers glutathione and cysteine on the inactivation of Yersinia enterocolitica in a red blood cell sample was examined. PRBCs were prepared in Adsol and spiked with Yersinia (California Department of Health Services, Microbial Disease Laboratory, Berkeley, Calif.), a common gram negative bacterial contaminant of blood. Samples were prepared with 150 μM PIC-1 and quencher as shown in Table 7. PIC-1 was added approximately 5 minutes after the quenchers. After a 4 hour incubation at room temperature, the titer of the bacteria was determined by plating dilutions on nutrient agar and culturing overnight at 37° C.

Table 7 shows the effects of GSH and cysteine on inactivation of Yersinia with 150 μM PIC-1. Neither glutathione nor cysteine alone at a concentration of 16 mM had any effect on the titer of Yersinia (samples 3 and 10). There was, however, a dose-dependent decrease in inactivation with the quenchers. The inactivation was inhibited by 4 to 4.5 logs with 16 mM quencher (samples 9 and 16), but the inhibition was less than 1 log with 2 mM quencher (samples 6 and 13).

TABLE 7

| Sample | PIC-1 | Quencher | Log Titer | Log Kill |
|---|---|---|---|---|
| 1 | none | none | 7.4 | — |
| 2 | 150 μM | none | 2.3 | 5.1 |
| Glutathione Samples | | | | |
| 3 | none | 16 mM GSH | 7.4 | 0 |
| 4 | 150 μM | 0.5 mM GSH | 3.0 | 4.4 |
| 5 | 150 μM | 1 mM GSH | 3.0 | 4.4 |
| 6 | 150 μM | 2 mM GSH | 3.3 | 4.1 |
| 7 | 150 μM | 4 mM GSH | 4.8 | 2.6 |
| 8 | 150 μM | 8 mM GSH | 6.1 | 1.3 |
| 9 | 150 μM | 16 mM GSH | 6.8 | 0.6 |
| Cysteine Samples | | | | |
| 10 | none | 16 mM Cys | 7.4 | 0 |
| 11 | 150 μM | 0.5 mM Cys | 2.9 | 4.5 |
| 12 | 150 μM | 1 mM Cys | 2.4 | 5.0 |
| 13 | 150 μM | 2 mM Cys | 3.2 | 4.2 |
| 14 | 150 μM | 4 mM Cys | 4.3 | 3.1 |
| 15 | 150 μM | 8 mM Cys | 6.9 | 0.5 |
| 16 | 150 μM | 16 mM Cys | 6.4 | 0.9 |

EXAMPLE 8

Use of Glutathione as a Quencher in the Inactivation of Staphylococcus epidermidis.

The effects of glutathione on the inactivation of Staphylococcus epidermidis (California Department of Health Services, Microbial Disease Laboratory, Berkeley, Calif.) in a red blood cell sample was examined. PRBCs were prepared in Adsol and spiked with S. epidermidis. Samples were prepared with 75 μM PIC-1 and the quencher, glutathione, as shown in Table 8. PIC-1 was added approximately 5 minutes after the quencher. After a 4 hour incubation at room temperature, the titer of the bacteria was determined by plating dilutions on nutrient agar and culturing overnight at 37° C.

Table 8 illustrates inactivation of *Staphylococcus epidermidis* with 75 µM PIC-1 and varying amounts of GSH. The results presented in Table 8 are consistent with the observation that glutathione inhibits bacterial inactivation to some degree. *S. epidermidis* apparently was less sensitive to glutathione quenching than Yersinia.

TABLE 8

| Sample | PIC-1 | GSH (mM) | Log Titer | Log Kill |
|---|---|---|---|---|
| 1 | None | none | 7.5 | — |
| 2 | 75 µM | none | 2.5 | 5.0 |
| 3 | None | 16 | 7.5 | 0 |
| 4 | 75 µM | 1 | 3.3 | 4.2 |
| 5 | 75 µM | 2 | 3.5 | 4.0 |
| 6 | 75 µM | 3 | 3.6 | 3.9 |
| 7 | 75 µM | 4 | 4.2 | 3.3 |
| 8 | 75 µM | 8 | 4.6 | 2.9 |
| 9 | 75 µM | 16 | 5.0 | 2.5 |

At a concentration of 1 to 4 mM, the quenchers diminish bacterial kill only modestly and 3 logs or greater of bacteria can be inactivated.

EXAMPLE 9

Study of the Effects of Quenchers on Reducing Undesired Side Reactions of Pathogen Inactivating Compounds in Materials Comprising Red Blood Cells.

The effects of glutathione and cysteine on IgG, albumin and pathogen inactivating compound binding to red cells was examined. Treatment of red blood cells with some pathogen inactivating compounds including a nucleic acid binding ligand and a reactive group such as a mustard group, such as PIC-1, can lead to low level, covalent binding of IgG to the surface of red cells. The amount of IgG is generally below levels required to create a positive result in the Direct Antiglobulin Test (DAT) (Walker, R. H., ed., *Technical Manual*, 10th Ed., American Association of Blood Banks, Arlington, Va., 1990). However, inclusion of a quencher can reduce or eliminate protein binding. Furthermore, using a polyclonal antibody mixture that recognizes the acridine moiety of PIC-1, binding of pathogen inactivating compound to the red cells surface is reduced when a quencher is included.

PRBCs were prepared at a hematocrit of 60% in Adsol. Prior to treatment with PIC-1, either glutathione or cysteine was added to concentrations between 0.5 and 16 mM, and the samples were mixed. PIC-1 was added to 1 mM, and the samples were incubated for 20 hours at room temperature. After incubation, twenty microliters of each sample were washed three times with 1 mL of blood bank saline and resuspended in a final volume of 0.4 mL.

Anti-acridine antibodies were prepared as described in Harlow and Lane, "Antibodies, a Laboratory Manual, Cold Spring Harbor Laboratory," 1988, the disclosure of which is incorporated herein. Goat anti-mouse IgG and anti-human albumin antibodies were obtained from Caltag, Burlingame, Calif.

For the analysis, 50 µL aliquots of diluted, washed red cells were aliquoted into four tubes and incubated with anti-human IgG, anti-human albumin, or anti-acridine antibodies for 30 min at 37° C. After incubation, samples were washed once with 1.0 mL of blood bank saline. The anti-human antibodies were covalently labeled with fluorescein and samples were analyzed directly using a flow cytometer. To detect the anti-acridine antibody, the samples were washed a second time and then incubated with a fluorescein-labeled goat anti-mouse IgG for 30 min at 37° C. Samples were washed as before prior to analysis.

For analysis, samples were diluted 1:1 into Haemaline 2 (Biochem Immunosystems, Allentown, Pa.) solution and analyzed in a FACScan (Becton-Dickinson, San Jose, Calif.) with the scattering settings optimized for red cell discrimination. Twenty thousand fluorescence events were collected per sample.

Table 9 illustrates the results showing the effect of glutathione and cysteine on IgG, albumin and acridine binding to red cells. Treatment with PIC-1 alone caused a clear increase in IgG, albumin and acridine signals (samples 1 and 2). Incubation with either 16 mM glutathione or cysteine did not alter the fluorescence compared to the untreated sample (samples 3 and 10, respectively). Treatment with PIC-1 in the presence of either quencher caused a dose-dependent decrease in the level of IgG, albumin and acridine binding. Both IgG and albumin binding appeared to be at background levels in the presence of ≧2 mM quencher (samples 6 and 13). Acridine binding, in contrast, was dependent on quencher concentration over the entire range tested. Even 16 mM glutathione or cysteine did not completely abrogate the acridine signal. With 4 mM glutathione, the acridine signal decreased 53-fold (sample 2 vs. sample 7); with 4 mM cysteine, the acridine signal decreased 83-fold (sample 2 vs. sample 14). In a parallel study using 0.3 mM PIC-1, similar trends were seen using glutathione although the initial level of binding of proteins and acridine was reduced due to the lower concentration of PIC-1.

TABLE 9

| | | | FACScan Fluorescence Mean fluorescence units | | |
|---|---|---|---|---|---|
| Sample | PIC-1 (mM) | Quencher (mM) | IgG | Albumin | Acridine |
| Positive and Negative Controls | | | | | |
| 1 | none | none | 3.1 | 5.0 | 4.2 |
| 2 | 1.0 | none | 14.8 | 13.2 | 3184 |
| Glutathione Samples | | | | | |
| 3 | none | 16 | 3.1 | 4.4 | 4.3 |
| 4 | 1.0 | 0.5 | 9.8 | 8.6 | 2095 |
| 5 | 1.0 | 1 | 5.2 | 5.8 | 898 |
| 6 | 1.0 | 2 | 3.0 | 5.0 | 169 |
| 7 | 1.0 | 4 | 3.4 | 4.5 | 60 |
| 8 | 1.0 | 8 | 4.1 | 4.7 | 25 |
| 9 | 1.0 | 16 | 4.5 | 4.0 | 18 |
| Cysteine Samples | | | | | |
| 10 | none | 16 | 3.6 | 3.5 | 4.1 |
| 11 | 1.0 | 0.5 | 6.6 | 7.0 | 1386 |
| 12 | 1.0 | 1 | 5.3 | 5.1 | 462 |
| 13 | 1.0 | 2 | 3.8 | 4.2 | 180 |
| 14 | 1.0 | 4 | 6.0 | 4.0 | 38 |
| 15 | 1.0 | 8 | 3.6 | 4.0 | 19 |
| 16 | 1.0 | 16 | 3.6 | 3.3 | 12 |

EXAMPLE 10

Study of the Effects of Glutathione on Properties of PIC-1 Treated, Stored PRBCs To determine any effects of glutatlione on the properties of red cells, the following experiment was performed in duplicate. Four units of ABO-matched whole blood were pooled, mixed and then redistributed into four blood bags to create identical 500 mL units. PRBCs were prepared using Adsol as the additive solution. Within 20 hours of receipt, units of whole blood received from the Sacramento Blood Bank are centrifuged at 3800 rpm for 5 minutes and the plasma is expressed into another container. The % hematocrit is measured by filling a capillary tube with the blood sample and spinning for 5 minutes. The volume taken up by the red cells is compared to a calibration curve. 94 mL of Adsol is added. Final hematocrit ranged from 50 to 53 percent depending on the treatment.

In each experiment, four conditions were examined: (1) Control, no PIC-1 and no glutathione; (2) 3 mM glutathione only; (3) 0.3 mM PIC-1 only; and (4) 0.3 mM PIC-1 plus 3 mM glutathione. All units including the control were incubated at 20° C. for 14 hours. The PRBCs were then transferred to 4° C. storage for the duration. Samples were taken immediately following treatment and on about a weekly basis thereafter for analysis. Results for 2,3-DPG, ATP and hemolysis are summarized in Tables 10 and 11. These data demonstrate no significant difference between any of the treatments compared to control. Measurements of extracellular potassium, intracellular glutathione, osmotic fragility, glucose consumption and lactate production also confirmed that glutathione, either alone or with PIC-1, does not significantly alter red cell in vitro properties.

Extracellular potassium levels were measured using a Ciba Corning Model 614 $K^+/Na^+$ Analyzer (Ciba Corning Diagnostics Corp., Medford, Mass.). Hemolysis was measured as described in Hogman et al., *Transfusion* 31: 26–29 (1991). Intracellular glutathione was measured as described in Beutler, "Red Cell Metabolism," Grune and Stratton, 3rd ed., 1984. 2,3-DPG and ATP were measured using Sigma procedures No. 665 and 366, respectively (Sigma, St. Louis, Mo.). Glucose consumption and lactate production were measured using Sigma procedure Nos. 115 and 735, respectively (Sigma, St. Louis, Mo.). Osmotic fragility was measured as described in Beutler el cl., *Blood*, Vol. 59 (1982).

TABLE 10

| Assay | Sample | Day 1 | Day 7 | Day 14 | Day 28 | Day 42 |
|---|---|---|---|---|---|---|
| 2,3-DPG | Control | 1.18 | 0.006 | 0.12 | n.d.* | n.d. |
| (µmol/mL) | GSH | 1.21 | 0.37 | 0 | n.d. | n.d. |
| | PIC-1 | 1.23 | 0.25 | 0.06 | n.d. | n.d. |
| | PIC-1/GSH | 1.16 | 0.29 | 0.02 | n.d. | n.d. |
| ATP | Control | 78.8 | 80.1 | 74.5 | 60.1 | 42.1 |
| (µmol/dL Hb) | GSH | 79.8 | 83.9 | 79.8 | 63.6 | 42.5 |
| | PIC-1 | 79.0 | 80.3 | 75.5 | 62.6 | 41.7 |
| | PIC-1/GSH | 80.1 | 81.3 | 77.6 | 63.0 | 44.5 |
| Hemolysis (%) | Control | 0.05 | 0.07 | 0.15 | 0.25 | 0.37 |
| | GSH | 0.04 | 0.07 | 0.16 | 0.24 | 0.33 |
| | PIC-1 | 0.06 | 0.08 | 0.15 | 0.24 | 0.33 |
| | PIC-1/GSH | 0.04 | 0.08 | 0.16 | 0.23 | 0.29 |

*n.d. = not done

TABLE 11

| Assay | Sample | Day 1 | Day 7 | Day 14 | Day 28 | Day 42 |
|---|---|---|---|---|---|---|
| 2,3-DPG | Control | 0.78 | 0.09 | n.d.* | n.d. | n.d. |
| (µmol/mL) | GSH | 0.69 | 0 | n.d. | n.d. | n.d. |
| | PIC-1 | 0.77 | 0.10 | n.d. | n.d. | n.d. |
| | PIC-1/GSH | 0.73 | 0.22 | n.d. | n.d. | n.d. |
| ATP | Control | 87.8 | 84.6 | 75.5 | 58.1 | 42.5 |
| (µmol/dL Hb) | GSH | 90.3 | 87.2 | 81.1 | 61.0 | 43.1 |
| | PIC-1 | 84.0 | 77.0 | 72.0 | 55.8 | 41.0 |
| | PIC-1/GSH | 87.0 | 82.5 | 75.7 | 58.9 | 42.7 |
| Hemolysis (%) | Control | 0.06 | 0.12 | 0.21 | 0.44 | 0.72 |
| | GSH | 0.06 | 0.11 | 0.18 | 0.31 | 0.56 |
| | PIC-1 | 0.07 | 0.13 | 0.19 | 0.31 | 0.46 |
| | PIC-1/GSH | 0.06 | 0.10 | 0.17 | 0.26 | 0.35 |

*n.d. not done

EXAMPLE 11

Study of Recovery and Survival of Mouse RBCs treated with GSH.

The effect of 0.6 mM PIC-2 with and without 6.0 mM GSH on the in vivo recovery and survival of biotin labeled murine red blood cells (RBCs) was studied. Mouse RBCs were labeled and then treated with PIC-2, PIC-2+glutathione, or glutathione only. Treated, labeled cells were infused into recipients. The circulation of these cells was followed over 36 days by flow cytometry. No difference was observed in the recovery or lifespan of any of the treated RBCs compared to label-only controls. The data demonstrate that glutathione in the treatment is compatible with in vivo RBC function and that PIC-2 treatment itself does not damage red cells.

Donor mice (BALB/c males) were injected with 0.1 mg NHS (N-hydroxysuccinimide) Biotin (Pierce, Rockford, Ill.) on Days 1 and 2. At one hour after the second injection the labeling efficiency was checked by reacting a small volume of biotin labeled whole blood from each mouse with a Streptavidin, R-phycoerythrin conjugate (Molecular Probes, Eugene Oreg.) and then determining the percentage of fluorescent cells on the FACScan (Becton-Dickinson, San Jose, Calif.). All mice having>90% labeled RBCs were used as donor mice.

Blood was taken from donor mice by cardiac puncture and spun once at 1282xg for six minutes. The plasma was removed, and the PRBCs incubated for 14 hours at room temperature (RT)±0.6 mM PIC-2±6.0 mM GSH. The following morning the RBCs were washed and resuspended in HBSS (Hanks Buffered Salt Solution, Sigma, St. Louis, Mo.). Percent biotin labeling of the washed RBCs were determined as above. The total number of RBCs was determined by doing a CBC (Complete blood cell count) on a cell counter (Complete Blood Count Cell Counter, Biochem Immunosystems, Allentown, Pa.).

The washed RBCs then were transfused into the recipient mice (BALB/c females.) Each mouse received≅800×10⁶ biotin labeled RBCs. Each mouse was weighed at the time of transfusion, and the true percentage of labeled RBC/mouse was calculated based on the weight of the mouse, its RBC count as determined by a CBC, and the percentage of labeled RBCs transfused determined as above.

The percent survival of the labeled RBC was determined at 1 hr, and day 1–40. Results were normalized by using the percent survival at one hour=100%. True percent recovery of labeled RBCs at one hour for all mice was 105.8±17.5%. Results were normalized to % survival at one hour=100% to allow for differences in the efficiency of the i.v. labeled RBC injection.

The PIC-2 treated RBC survival was substantially the same as control throughout the experiment. The average mean survival values are provided in FIG. 1. The data suggest that treatment with PIC-2, either with or without glutathione, did not have a significant effect on RBC survival. Thus, glutathione is compatible with the in vivo circulation of red blood cells after treatment.

What is claimed is:

1. A method of quenching undesired side reactions of a pathogen inactivating compound in a blood product, the method comprising:

treating the blood product with a pathogen inactivating compound comprising a nucleic acid binding ligand and a functional group which is, or which forms, an electrophilic group;

wherein the pathogen inactivating compound does not require photoactivation to inactivate a pathogen; and treating the blood product with a quencher comprising a nucleophilic group that can covalently react with the electrophilic group, wherein the quencher is present in an amount sufficient to reduce the level of side reactions and wherein the pathogen inactivating compound penetrates the pathogen relative to the quencher in an amount capable of inactivating the pathogen before it is quenched.

2. The method of claim 1, wherein the electrophilic group is cationic.

3. The method of claim 2, wherein the electrophilic group is an aziridinium ion.

4. The method of claim 1 wherein the method comprises treating the blood product with the pathogen inactivating compound and the quencher in vitro.

5. The method of claim 1 wherein the method comprises treating the blood product with the pathogen inactivating compound and the quencher ex vivo.

6. The method of claim 1 wherein the electrophilic group reacts with a nucleic acid to form a covalent bond with the nucleic acid.

7. The method of claim 6, wherein the functional group is a mustard group that is capable of reacting in situ to form the electrophilic group.

8. The method of claim 6, wherein the pathogen inactivating compound further comprises a frangible linker linking the functional group and the nucleic acid binding ligand.

9. The method of claim 6, wherein the pathogen inactivating compound comprises a nucleic acid binding ligand selected from the group consisting of furocoumarins, furocoumarin derivatives, acridines and acridine derivatives; and wherein the functional group is a mustard group.

10. The method of claim 1, wherein the pathogen inactivating compound is selected from the group consisting of β-alanine, N-(acridin-9-yl), 2-[bis(2-chloroethyl)amino] ethyl ester and quinacrine mustard.

11. The method of claim 1, wherein the nucleophilic group is selected from the group consisting of a thiol, thioacid, dithoic acid, phosphate, thiophosphate, thiosulfate, and an amine.

12. The method of claim 11, wherein the nucleophilic group is a thiol.

13. The method of claim 12, wherein the quencher is selected from the group consisting of glutathione, N-acetylcysteine, cysteine, mercaptoethanesulfonate salts, and dimercaprol.

14. The method of claim 13, wherein the quencher is glutathione.

15. The method of claim 14, wherein the concentration of glutathione is about 0.5 to 30 mM.

16. The method of claim 1, wherein the blood product comprises a material selected from the group consisting of whole blood, red blood cells, and platelets.

17. The method of claim 1, wherein the pathogen inactivating compound and the quencher are incubated with the blood product for at least about 1 to 48 hours.

18. The method of claim 1, wherein the concentration of pathogen inactivating compound is about 0.1 µM to 5 mM.

19. The method of claim 1, wherein the concentration of pathogen inactivating compound is sufficient to inactivate at least about 3 to 6 logs of the pathogen in the material.

20. The method of claim 1, wherein the quencher reduces the inactivation of the pathogen by the pathogen inactivating compound by no greater than about 3 logs in comparison to a control pathogen inactivation conducted in the absence of the quencher.

21. The method of claim 1, wherein the quencher reduces the inactivation of a viral pathogen by the pathogen inactivating compound by no greater than about 1 log in comparison to a control pathogen inactivation conducted in the absence of the quencher.

22. The method of claim 1, wherein the quencher comprises a solid support material comprising the nucleophilic group.

23. The method of claim 1, wherein the quencher is added to the blood product prior to, or simultaneously with, the addition of the pathogen inactivating compound.

24. A method for quenching undesired side reactions of a pathogen inactivating compound in a material comprising red blood cells, the method comprising:

treating a material comprising red blood cells with a pathogen inactivating compound comprising a nucleic acid binding ligand and a functional group which is, or which forms, an electrophilic group;

wherein the pathogen inactivating compound does not require photoactivation to inactivate a pathogen; and treating the material with a quencher comprising a nucleophilic group that can covalently react with the electrophilic group, wherein the quencher is present in an amount sufficient to reduce the level of side reactions and wherein the pathogen inactivating compound penetrates the pathogen relative to the quencher in an amount capable of inactivating the pathogen before it is quenched.

25. The method of claim 24, wherein the electrophilic group is cationic.

26. The method of claim 25, wherein the electrophilic group is an aziridinium ion.

27. The method of claim 24, wherein the method comprises treating the material with the pathogen inactivating compound and the quencher in vitro.

28. The method of claim 24, wherein the method comprises treating the material with the pathogen inactivating compound and the quencher ex vivo.

29. The method of claim 24, wherein the electrophilic group reacts with a nucleic acid to form a covalent bond with the nucleic acid.

30. The method of claim 29, wherein the functional group is a mustard group that is capable of reacting in situ to form the electrophilic group.

31. The method of claim 29, wherein the pathogen inactivating compound further comprises a frangible linker linking the functional group and the nucleic acid binding ligand.

32. The method of claim 29, wherein the pathogen inactivating compound comprises a nucleic acid binding ligand selected from the group consisting of furocoumarins, furocoumarin derivatives, acridines and acridine derivatives; and wherein the functional group is a mustard group.

33. The method of claim 24, wherein the pathogen inactivating compound is selected from the group consisting of β-alanine, N-(acridin-9-yl), 2-[bis(2-chloroethyl)amino] ethyl ester and quinacrine mustard.

34. The method of claim 24 wherein the nucleophilic group is selected from the group consisting of a thiol, thioacid, dithoic acid, phosphate, thiophosphate, thiosulfate and an amine.

35. The method of claim 34, wherein the nucleophilic group is a thiol group.

36. The method of claim 35, wherein the method comprises treating the material with a quencher selected from the group consisting of glutathione, N-acetylcysteine, cysteine, mercaptoethanesulfonate salts, and dimercaprol.

37. The method of claim 36, wherein the quencher is glutathione.

38. The method of claim 37, wherein the concentration of glutathione is about 0.5 to 30 mM.

39. The method of claim 24, wherein the pathogen inactivating compound and the quencher are incubated with the material for at least about 1 to 48 hours.

40. The method of claim 24, wherein the concentration of pathogen inactivating compound is about 0.1 μM to 5 mM.

41. The method of claim 24, wherein the concentration of pathogen inactivating compound is sufficient to inactivate at least about 3 to 6 logs of the pathogen in the material.

42. The method of claim 24, wherein the quencher reduces the inactivation of the pathogen by the pathogen inactivating compound by no greater than about 3 logs in comparison to a control pathogen inactivation conducted in the absence of the quencher.

43. The method of claim 24, wherein the quencher reduces the inactivation of a viral pathogen by the pathogen inactivating compound by no greater than about 1 log in comparison to a control pathogen inactivation conducted in the absence of the quencher.

44. The method of claim 24, wherein the treatment results in less than 3% hemolysis of the red blood cells after storage for 28 days.

45. The method of claim 24, wherein the material has a hematocrit of about 30–85%.

46. The method of claim 24, wherein the material comprises packed red blood cells.

47. The method of claim 24, wherein the quencher comprises a solid support material comprising the nucleophilic group.

48. The method of claim 24, wherein the quencher is added to the material prior to, or simultaneously with, the addition of the pathogen inactivating compound.

49. The method of claim 24, wherein the method comprises treating the material with an effective amount of the pathogen inactivating compound and the quencher to inactivate at least 2 logs of the pathogen, and wherein red blood cell function is not substantially damaged by the treatment.

50. The method of claim 24, wherein hemolysis of the red blood cells is less than 3% after 28 days of storage after treatment.

51. The method of claim 50, wherein the method comprises treating the material with an effective amount of the pathogen inactivating compound and the quencher to inactivate at least 2 logs of the pathogen.

52. The method of claim 24, wherein, after the treatment, the material is suitable for introduction into an individual.

53. The method of claim 52, wherein the method further comprises transfusing the treated material comprising red blood cells into an individual in need thereof.

54. The method of claim 53, wherein the concentration of at least one of the pathogen inactivating compound and the quencher in the material is reduced after the treatment and before transfusion.

55. The method of claim 23, wherein the pathogen is selected from the group consisting of prokaryotic and eukaryotic organisms and lipid coated viruses.

56. The method of claim 24, wherein the pathogen is selected from the group consisting of prokaryotic and eukaryotic organisms and lipid coated viruses.

57. A method of quenching undesired side reactions of a pathogen inactivating compound in a biological material, the method comprising:
    treating a biological material with β-alanine, N-(acridin-9-yl), 2-[bis(2-chloroethyl)amino]ethyl ester; and
    treating the biological material with a quencher comprising a nucleophilic group that can covalently react with the β-alanine, N-(acridin-9-yl), 2-[bis(2-chloroethyl)amino]ethyl ester;
    wherein the β-alanine, N-(acridin-9-yl), 2-[bis(2-chloroethyl)amino]ethyl ester is present in a sufficient amount such that it traverses the pathogen membrane relative to the quencher such that a pathogen-inactivating amount of the pathogen inactivating compound traverses the pathogen membrane before it is quenched.

58. The method of claim 57, wherein the nucleophilic group is selected from the group consisting of a thiol, thioacid, dithoic acid, phosphate, thiophosphate, thiosulfate and an amine.

59. The method of claim 58, wherein the nucleophilic group is a thiol.

60. The method of claim 59, wherein the quencher is selected from the group consisting of glutathione, N-acetylcysteine, cysteine, mercaptoethanesulfonate salts, and dimercaprol.

61. The method of claim 60, wherein the quencher is glutathione.

62. The method of claim 61, wherein the concentration of glutathione is about 0.5 to 30 mM.

63. The method of claim 57, wherein the biological material comprises a material selected from the group consisting of whole blood, red blood cells, plasma, and platelets.

64. The method of claim 63, wherein the biological material comprises red blood cells.

65. The method of claim 64, wherein the material comprises packed red blood cells.

66. The method of claim 64, wherein red blood cell function is not substantially damaged after the treatment.

67. The method of claim 64, wherein the biological material has a hematocrit of about 30–85%.

68. The method of claim 64, wherein at least 2 logs of a pathogen are inactivated, and wherein red blood cell function is not substantially damaged by the treatment.

69. The method of claim 64, wherein hemolysis of the red blood cells is less than 3% after 28 days of storage after treatment.

70. The method of claim 69, wherein the method comprises treating the material with an effective amount of β-alanine, N-(acridin-9-yl), 2-[bis(2-chloroethyl)amino] ethyl ester and the quencher to inactivate at least 2 logs of a pathogen.

71. The method of claim 63, wherein, after the treatment, the biological material is suitable for introduction into an individual.

72. The method of claim 71, wherein the method further comprises transfusing the treated material into an individual in need thereof.

73. The method of claim 72, wherein the concentration of at least one of the pathogen inactivating compound and the quencher in the material is reduced after the treatment and before transfusion.

74. The method of claim 57 wherein the method comprises treating the biological material with β-alanine, N-(acridin-9-yl), 2-[bis(2-chloroethyl)amino]ethyl ester and the quencher in vitro.

75. The method of claim 57 wherein the method comprises treating the biological material with β-alanine, N-(acridin-9-yl), 2-[bis(2-chloroethyl)amino]ethyl ester and the quencher ex vivo.

76. The method of claim 57, wherein β-alanine, N-(acridin-9-yl), 2-[bis(2-chloroethyl)amino]ethyl ester and the quencher are incubated with the material for at least about 1 to 48 hours.

77. The method of claim 57, wherein the concentration of β-alanine, N-(acridin-9-yl), 2-[bis(2-chloroethyl)amino]ethyl ester is about 0.1 µM to 5 mM.

78. The method of claim 57, wherein the concentration of β-alanine, N-(acridin-9-yl), 2-[bis(2-chloroethyl)amino]ethyl ester is sufficient to inactivate at least about 3 to 6 logs of a pathogen in the material.

79. The method of claim 57, wherein the quencher reduces the inactivation of a pathogen by β-alanine, N-(acridin-9-yl), 2-[bis(2-chloroethyl)amino]ethyl ester by no greater than about 3 logs in comparison to a control pathogen inactivation conducted in the absence of the quencher.

80. The method of claim 57, wherein the quencher reduces the inactivation of a viral pathogen by β-alanine, N-(acridin-9-yl), 2-[bis(2-chloroethyl)amino]ethyl ester by no greater than about 1 log in comparison to a control pathogen inactivation conducted in the absence of the quencher.

81. The method of claim 57, wherein the quencher comprises a solid support material comprising the nucleophilic group.

82. The method of claim 57, wherein the quencher is added to the material prior to, or simultaneously with, the addition of β-alanine, N-(acridin-9-yl), 2-[bis(2-chloroethyl)amino]ethyl ester.

83. The method of claim 57, wherein the pathogen is selected from the group consisting of prokaryotic and eukaryotic organisms and lipid coated viruses.

84. A method of quenching undesired side reactions of a pathogen inactivating compound in a biological material, the method comprising:
   treating a biological material with a pathogen inactivating compound comprising a functional group which is, or which forms, an electrophilic group and which is capable of forming a covalent bond with a nucleic acid; wherein the pathogen inactivating compound further comprises a nucleic acid binding ligand and a frangible linker covalently linking the nucleic acid binding ligand and the functional group; and
   treating the biological material with a quencher comprising a nucleophilic group that can covalently react with the electrophilic group;
   wherein the quencher is present in an amount sufficient to reduce the level of side reactions and wherein the pathogen inactivating compound penetrates the pathogen relative to the quencher in an amount capable of inactivating a pathogen before it is quenched.

85. The method of claim 84, wherein the pathogen inactivating compound displays hydrolysis of the frangible linker of between about 40% and about 99% after 100 minutes in aqueous solution at pH 8 and 37° C.

86. The method of claim 84, wherein the linker does not contain an amide group.

87. The method of claim 84, wherein the electrophilic group is cationic.

88. The method of claim 87, wherein the electrophilic group is an aziridinium ion.

89. The method of claim 84, wherein the functional group is a mustard group that is capable of reacting in situ to form the electrophilic group.

90. The method of claim 84, wherein the nucleic acid binding ligand is selected from the group consisting of furocoumarins, furocoumarin derivatives, acridines and acridine derivatives; and
   wherein the functional group is a mustard group.

91. The method of claim 84, wherein the pathogen inactivating compound is β-alanine, N-(acridin-9-yl), 2-[bis(2-chloroethyl)amino]ethyl ester.

92. The method of claim 84, wherein the nucleophilic group is selected from the group consisting of a thiol, thioacid, dithoic acid, phosphate, thiophosphate, thiosulfate and an amine.

93. The method of claim 92, wherein the nucleophilic group is a thiol.

94. The method of claim 93, wherein the quencher is selected from the group consisting of glutathione, N-acetylcysteine, cysteine, mercaptoethanesulfonate salts, and dimercaprol.

95. The method of claim 94, wherein the quencher is glutathione.

96. The method of claim 95, wherein the concentration of glutathione is about 0.5 to 30 mM.

97. The method of claim 84, wherein the biological material comprises a material selected from the group consisting of whole blood, red blood cells, plasma, and platelets.

98. The method of claim 97, wherein the biological material comprises red blood cells.

99. The method of claim 98, wherein the material comprises packed red blood cells.

100. The method of claim 98, wherein red blood cell function is not substantially damaged after the treatment.

101. The method of claim 98, wherein the biological material has a hematocrit of about 30–85%.

102. The method of claim 98, wherein the method comprises treating the material with an effective amount of the pathogen inactivating compound and the quencher to inactivate at least 2 logs of a pathogen, and wherein red blood cell function is not substantially damaged by the treatment.

103. The method of claim 98, wherein hemolysis of the red blood cells is less than 3% after 28 days of storage after treatment.

104. The method of claim 103, wherein the method comprises treating the material with an effective amount of the pathogen inactivating compound and the quencher to inactivate at least 2 logs of a pathogen.

105. The method of claim 97, wherein, after the treatment, the biological material is suitable for introduction into an individual.

106. The method of claim 105, wherein the method further comprises transfusing the treated material into an individual in need thereof.

107. The method of claim 106, wherein the concentration of at least one of the pathogen inactivating compound and the quencher in the material is reduced after the treatment and before transfusion.

108. The method of claim 84, wherein the pathogen is selected from the group consisting of prokaryotic and eukaryotic organisms and lipid coated viruses.

109. The method of claim 84 wherein the method comprises treating the biological material with the pathogen inactivating compound and the quencher in vitro.

110. The method of claim 84 wherein the method comprises treating the biological material with the pathogen inactivating compound and the quencher ex vivo.

111. The method of claim 84, wherein the pathogen inactivating compound and the quencher are incubated with the material for at least about 1 to 48 hours.

112. The method of claim 84, wherein the concentration of the pathogen inactivating compound is about 0.1 $\mu$M to 5 mM.

113. The method of claim 84, wherein the pathogen inactivating compound is sufficient to inactivate at least about 3 to 6 logs of a pathogen in the material.

114. The method of claim 84, wherein the quencher reduces the inactivation of a pathogen by the pathogen inactivating compound by no greater than about 3 logs in comparison to a control pathogen inactivation conducted in the absence of the quencher.

115. The method of claim 84, wherein the quencher reduces the inactivation of a viral pathogen by the pathogen inactivating compound by no greater than about 1 log in comparison to a control pathogen inactivation conducted in the absence of the quencher.

116. The method of claim 84, wherein the quencher comprises a solid support material comprising the nucleophilic group.

117. The method of claim 84, wherein the quencher is added to the material prior to, or simultaneously with, the addition of the pathogen inactivating compound.

\* \* \* \* \*